United States Patent
Tennants et al.

(10) Patent No.: US 10,716,839 B2
(45) Date of Patent: Jul. 21, 2020

(54) COMPOSITIONS AND METHODS FOR PRODUCING BACTERIAL CONJUGATE VACCINES

(71) Applicant: University of Maryland, Baltimore, Baltimore, MD (US)

(72) Inventors: Sharon M. Tennants, Baltimore, MD (US); Raphael Simon, Baltimore, MD (US); Myron M. Levine, Columbia, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 15/566,333

(22) PCT Filed: Apr. 13, 2016

(86) PCT No.: PCT/US2016/027325
§ 371 (c)(1),
(2) Date: Oct. 13, 2017

(87) PCT Pub. No.: WO2016/168324
PCT Pub. Date: Oct. 20, 2016

(65) Prior Publication Data
US 2018/0099038 A1    Apr. 12, 2018

Related U.S. Application Data

(60) Provisional application No. 62/146,545, filed on Apr. 13, 2015.

(51) Int. Cl.
| | | |
|---|---|---|
| *A61K 39/112* | (2006.01) | |
| *A61K 39/385* | (2006.01) | |
| *A61K 39/02* | (2006.01) | |
| *C08B 37/00* | (2006.01) | |
| *A61K 39/00* | (2006.01) | |

(52) U.S. Cl.
CPC ........ *A61K 39/0275* (2013.01); *C08B 37/006* (2013.01); *A61K 39/0011* (2013.01); *A61K 2039/522* (2013.01); *A61K 2039/55583* (2013.01); *A61K 2039/55594* (2013.01); *A61K 2039/6031* (2013.01); *A61K 2039/6037* (2013.01); *A61K 2039/6087* (2013.01); *Y02A 50/482* (2018.01)

(58) Field of Classification Search
CPC ............ A61K 39/0275; A61K 39/0011; A61K 2039/6037; A61K 2039/522
See application file for complete search history.

(56) References Cited

U.S. PATENT DOCUMENTS

| | | | |
|---|---|---|---|
| 2003/0124634 | A1 | 7/2003 | Lam et al. |
| 2011/0274714 | A1* | 11/2011 | Levine ............... A61K 39/0275 424/194.1 |
| 2013/0078278 | A1 | 3/2013 | Kopecko et al. |
| 2013/0129776 | A1 | 5/2013 | Levine et al. |

FOREIGN PATENT DOCUMENTS

WO     2012061400     5/2012

OTHER PUBLICATIONS

Murray et al., Molecular Microbiology, 2003; 47(5): 1395-1406 (Year: 2003).*
Carter et al., Microbiology, 2009; 155: 3260-3269 (Year: 2009).*
Brady et al., BioProcess International, 2012; https://bioprocessintl.com/manufacturing/monoclonal-antibodies/carrier-protein-outsourcing-337128/ (Year: 2012).*
Finn, British Medical Bulletin, 2004; 70: 1-14 (Year: 2004).*
Cuadros et al., Infection and Immunity, 2004; 72(5): 2810-2816 (Year: 2004).*
Burrows et al., Journal of Bacteriology, 1997; 179(5): 1482-1489 (Year: 1997).*
International Search Report and Written Opinion for corresponding PCT Application PCT/US2016/027435, dated Aug. 11, 2016, pp. 1-13.
Chinchilla, M., et al., "Enhanced immunity to Plasmodium falciparum circumsporozoite protein (PfCSP) by using *Salmonella enterica* serovar Typhi expressing PICSP and a PfCSP-encoding DNA vaccine in a heterologous prime-boost strategy," Infect. Immun., May 2007, vol. 75, pp. 3769-3779.
Islam, S., et al., "Synthesis of bacterial polysaccharides via the Wzx/Wzy-dependent pathway," Can. J. Microbial. Sep. 2014, vol. 60, pp. 697-716.
McKenzie, G., et al., "Fast, easy and efficient: site-specific insertion of transgenes into enterobacterial chromosomes using Tn7 without need for selection of the insertion event," BMC Microbial., Apr. 2006, vol. 6, pp. 1-7.
Murray, G., et al., "Regulation of *Salmonella typhimurium* lipopolysaccha ride O antigen chain length is required for virulence; identification of FepE as a second Wzz," Mol. Microbial., Feb. 2003, vol. 47 , pp. 1395-1406.
(Continued)

*Primary Examiner* — Gary B Nickol
*Assistant Examiner* — Lakia J Jackson-Tongue
(74) *Attorney, Agent, or Firm* — Beusse Wolter Sanks & Maire; Eugene J. Molinelli; Martha Cassidy

(57) ABSTRACT

Longer chain antigenic O-polysaccharide chains for use as a hapten in conjugate vaccines can be produced in a controlled manner using recombinant Gram-negative bacteria that overexpress native or heterologous genes of the wzz family, for example wzzB. Bacteria expressing a chosen wzz gene have modified O-polysaccharide chain lengths, allowing the bacteria to produce lipopolysaccharides having the longer O-polysaccharides. The LPS produced by the bacteria can be hydrolyzed to form core-O-polysaccharide molecules that can be conjugated to a carrier molecule, for example flagellin, to produce a vaccine. The invention also provides recombinant bacteria producing the longer chain O-polysaccharides, the polysaccharide molecules, themselves, conjugated vaccines comprising the O-polysaccharides, pharmaceutical compositions and kits.

9 Claims, 12 Drawing Sheets

Specification includes a Sequence Listing.

(56) References Cited

OTHER PUBLICATIONS

Tennant, S., et al., "Engineering and preclinical evaluation of attenuated nontyphoidal Salmonella strains serving as live oral vaccines and as reagent strains," Infect. Immun., Aug. 2011, vol. 79, pp. 4175-4185.
"Cloning Vector pUC19: Product Information Sheet #V33202," MoBiTec, Dec. 1, 2013, pp. 1-3.
Bardotti, A., Averani, G., Berti, F., Berti, S., Carinci, V., et al. (2008) Physiochemical characterisation of glycoconjugate vaccines for prevention of meningococcal diseases. Vaccine 26: 2284-2296.
Carter, J., Jimenez, J., Zaldivar, M., Alvarez, S., Marolda, C., et al. (2009) The cellular level of O-antigen polymerase Wzy determines chain length regulation by WzzB and WzzpHS-2 in Shigella flexneri 2a. Microbiology 155: 3260-3269.
Cohen, D., Ashkenazi, S., Green, M., Gdalevich, M., Robin, G., et al. (1997) Double-blind vaccine-controlled randomised efficacy trial of an investigational Shigella sonnei conjugate vaccine in young adults. The Lancet 349: 155-159.
Darveau et al. J. (1983) Procedure for Isolation of bacterial Lipopolysaccharides from Both Smooth and Rough Pseudomonas aeruginosa and *Salmonella typhimurium* strains. Journal of Bacteriology, 155(2):831-838.
Datsenko, K., et al. (2000) One-step Inactivation of Chromosonal Genes in *Escherichia coli* K-12 using PCR products. Proceedings of the National Academy of Sciences. U.S.A. 97(12):6640-6645.
Kothari, S., et al., "Purification of O-specific polysaccharide from lipopolysaccharide produced by *Salmonella anterica* serovar Paratyphi A," Vaccine. 2014; 32(21):2457-62. Epub Mar. 12, 2014. http://dx.doi.org/10.1016/j.vaccine.2014.02.090.
Kubler-Kielb, J., Vinogradov, E., Mocca, C., Pozsgay, V., Coxon, B., et al. (2010) Immunochemical studies of Shigella flexneri 2a and 6, and Shigella dysenteriae type 1 O-specific polysaccharide-core fragments and their protein conjugates as vaccine candidates. Carbohydrate Research 345:1600-1608.
Lindberg, A.A., Le Minor, L. (1984) Serology of Salmonella. In: Bergan, T, editor. Methods in Microbiology: Academic Press. pp. 1-141.
Robbins, J., Kubler-Kielb, J., Vinogradov, E., Mocca, C., Pozsgay, V., et al. (2009) Synthesis, characterization, and immunogenicity in mice of Shigella sonnei O-specific oligosaccharide-core-protein conjugates. Proceedings of the National Academy of Sciences. U S A 106(19): 7974-7978.
Rondini, S. et al. (2011) Evaluation of the Immunogenicity and Biological Activity of the Citrobacter Freundii VI-CRM197 Conjugate as a Vaccine for *Salmonella enterica* Serovar Typhi. Clinical and Vaccine Immunology. 18 (3):460-468.
Simon, R., Tennant, S. Wang, J., Schmidlein, P., Lees, A., et al. (2011) *Salmonella enterica* serovar enteritidis core O-polysaccharide conjugated to H:g,m flagellin as a candidate vaccine for protection against invasive infection with *S. enteritidis*. Infection and Immunity 79(10): 4240-4249.
Svenson, S., Lindberg, A. (1981) Artificial Salmonella vaccines: *Salmonella typhimurium* O-antigen-specific oligosaccharide-protein conjugates elicit protective antibodies in rabbits and mice. Infection and Immunity 32(2): 490-496.
Watson, D., Robbins, J., Szu, S. (1992) Protection of mice against *Salmonella typhimurium* with an O-specific polysaccharide-protein conjugate vaccine. Infection and Immunity 60(11): 4679-4686.
Westphal, O., et al. (1965) Extraction with Phenol-Water and Further Applications of the Procedure. Ch. 25 Bacterial Lipopolysaccharides. Methods in Carbohydrate Chemistry. 5:83-91.
Zink, Phd, Gilbert L. (1980) Immunizing Agents and Diagnostic Antigens. Remingtons Pharmaceutical Sciences, Ch. 73:1334-1340.

\* cited by examiner

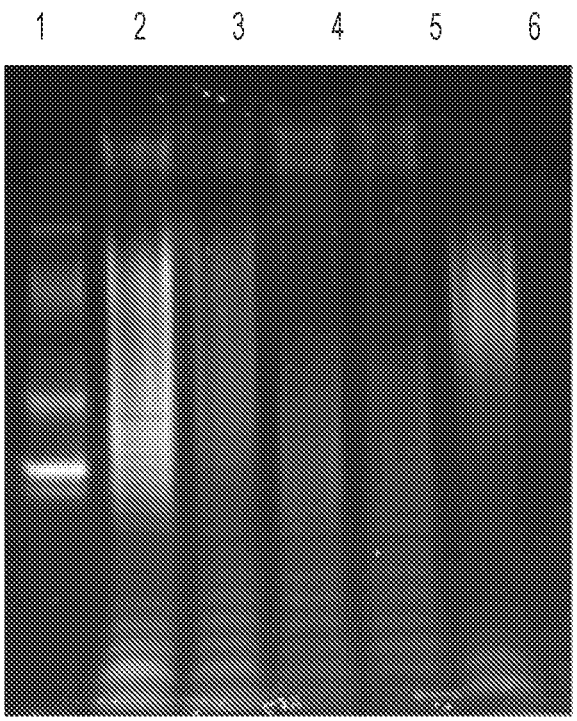
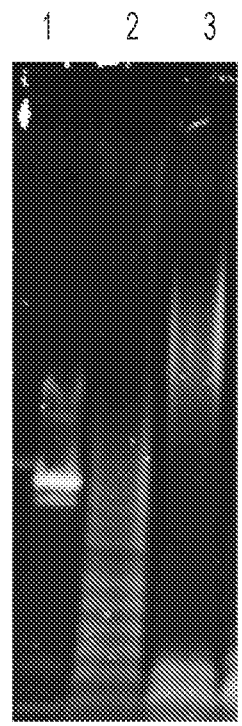
1. MWM
2. CVD 1943
3. CVD 1925
4. CVD 1902
5. CVD 1902 (pSE280)
6. CVD 1902 (pSE280-wzzB)
FIG. 4A
1. MWM
2. CVD 1902
3. CVD 1902 (pSEC10-wzzB)
FIG. 4B 1. CVD1208s (pSEC10)
2. CVD1208s (pSEC10_wzzB)
3. CVD1208s

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Synthetic primer: wzzBF-BamHI

<400> SEQUENCE: 1
aaaggatcca tgacagtgga tagttatacg                                30

<210> SEQ ID NO 2
<211> LENGTH: 31
<212> TYPE: DNA
<213> ORGANISM: Artificial Sequence
<220> FEATURE:
<223> OTHER INFORMATION: Synthetic primer: wzzB-PstI

<400> SEQUENCE: 2
aaactgcagt tacaaggctt ttggcttata g                              31

COMPOSITIONS AND METHODS FOR PRODUCING BACTERIAL CONJUGATE VACCINES

CROSS REFERENCE TO RELATED APPLICATIONS

This application is a 371 national stage application of PCT Application No. PCT/US2016/027325 filed Apr. 13, 2016 which claims the benefit of provisional application 62/146,545, entitled "Compositions and Methods for Producing Bacterial Conjugate Vaccines," filed Apr. 13, 2015, the entire contents of which are incorporated herein.

BACKGROUND

Bacterial capsular and outer membrane saccharides are abundant cell surface antigens that are generally accessible by antibodies and targets for protective immune responses. The surface carbohydrates of un-encapsulated Gram-negative bacteria (GNB) are lipopolysaccharides (LPS). LPS comprise a lipid A membrane anchor that links a single core polysaccharide to a polymer of O-polysaccharide (OPS) containing a number of repeated saccharide monomer units, which form short, intermediate, long or very long O-chains. While the core polysaccharide is mostly conserved within individual bacterial species, the O-polysaccharide can be variable and is used to distinguish serotypes.

Antibodies specific for the OPS of several important GNB human pathogens have protected against infection with the homologous pathogen in preclinical animal models [1,2] and clinical trials [3]. There is marked interest in the use of OPS as the basis of vaccines. However, isolated OPS are poorly immunogenic. Chemical linkage to protein carriers has improved their immunogenicity, and a functional boost response can be achieved by repeated administration of OPS conjugates. Despite their promise as vaccine antigens, the natural variability in polymer size represents a practical challenge in their commercial use. Longer chain and higher molecular weight saccharide haptens tend to be more immunogenic, but some bacterial strains produce the longer chains in lesser amounts, creating difficulties in developing different conjugation synthesis strategies, producing a uniform product, and producing high glycoconjugate immunogenicity. Size fractionation can be used to obtain the desired saccharide size; however, addition of a sizing step can introduce extraneous cost to the production process. Furthermore, the desired polysaccharide size may constitute only a minor proportion of the total saccharide population. A need exists for safe and efficient production of more numerous and longer OPS at less cost, for use in producing conjugate vaccines.

Wzz proteins are chain length regulators, expressed in the bacterial periplasm that control the activity of the Wzy OPS polymerase. The modal number of OPS monomer repeats produced by GNB using the Wzy LPS synthesis system is controlled by Wzz proteins. The protein structure and specificity of wzz family members varies between bacterial species. Some bacteria encode several different wzz genes, and their expression can be subject to control by growth phase and environmental conditions.

SUMMARY

The invention described herein relates to a method of controlling the length of and/or lengthening the O-polysaccharide chains produced by a Gram-negative bacterium in culture to produce bacterial LPS with longer, higher molecular weight O-polysaccharide chains. Embodiments of the invention include methods for increasing the production of intermediate-, long- and/or very long-chain OPS by overexpressing a wzz family gene product which can influence bacterial metabolism to produce longer chains. Such antigenic longer chain OPS haptens are thereby produced in greater quantity and at less cost than prior methods. Therefore, the invention described herein includes, at least in part, the following.

Embodiments of the invention include a method of manipulating the length of OPS produced by a Gram-negative bacterium in culture comprising overexpressing wzz family proteins from the Gram-negative bacterium in a homologous Gram-negative bacterial strain or in a heterologous Gram-negative bacterial strain to generate a high yield of large molecular weight lipopolysaccharides containing intermediate or long O-polysaccharide chains. A desired chain length is the one which produces maximal immunogenicity in the context of a given vaccine construct. Certain embodiments further comprise repressing wzz family gene products from the Gram-negative bacterium in a homologous Gram-negative bacterial strain or in a heterologous Gram-negative bacterial strain.

In preferred embodiments, the wzz family protein is selected from the group consisting of wzzB, wzz, $wzz_{SF}$, $wzz_{ST}$, fepE, $wZZ_{fepE}$, wzz, 1 and wzz2, most preferably wzzB.

In preferred embodiments of the method, the Gram-negative bacterium is selected from the group consisting of *Acinetobacter, Burkholderia, Bordetella, Campylobacter, Escherichia coli, Francisella, Haemophilus, Helicobacter, Pseudomonas, Salmonella enterica, Shigella, Vibrio,* and *Yersinia* species. More preferably, the Gram-negative bacterial strain is selected from the group consisting of *Salmonella enterica* serotype *Enteritidis* CVD 1943, *Salmonella enterica* serotype *Typhimurium* CVD 1925, *Salmonella enterica* serotype Paratyphi A CVD 1902, and *Shigella flexneri* CVD 1208S.

According to embodiments of the invention, the overexpression of the wzzB gene occurs from a high copy number plasmid, such as, for example, pSE280 or pUCP19. Alternatively, the overexpression of the wzzB gene occurs from a low copy number plasmid, such as, for example, pSEC10. In a further alternative embodiment, the overexpression of the wzz family gene occurs from the chromosome, where the endogenous wzz gene may or may not be deleted.

In highly preferred embodiments of the invention, the overexpression of wzzB shifts production of lipopolysaccharides containing intermediate chain length to liposaccharides containing long chain length.

Embodiments of the invention also include lipopolysaccharides produced by the methods described herein, preferably from the Gram-negative bacterium, *Salmonella enterica* serotype *Typhimurium*. Alternatively, the lipopolysaccharide produced by these methods is a Gram-negative strain selected from the group consisting of *Salmonella enterica* serotype *Typhimurium* CVD 1925, *Salmonella enterica* serotype Paratyphi A CVD 1902, and *Shigella flexneri* CVD 1208S. Therefore, embodiments of the invention also include a core-O-polysaccharide hapten purified from wzz family protein overexpressing Gram-negative bacteria, preferably *Salmonella enterica* serotype *Typhimurium* CVD 1925 or *Salmonella enterica* serotype Paratyphi A CVD 1902.

Further embodiments of the invention include a core-O-polysaccharide hapten purified from a Gram-negative bacterial strain overexpressing a wzz family protein for use as a vaccine antigen either as a conjugate or complexed vaccine. The wzz family protein preferably is wzzB. In addition, the invention encompasses embodiments such as a conjugate or complexed vaccine comprising one or more of these core-O-polysaccharide haptens, wherein the core-O-polysaccharide hapten is covalently linked or complexed to a carrier protein. The core-O-polysaccharide hapten and the carrier protein optionally are chemically conjugated or complexed using a cross-linker or polymer. In these conjugate vaccines, the carrier protein is from a homologous bacterial strain or a heterologous bacterial strain.

Other embodiments of the invention include an O-polysaccharide chain purified from a Gram-negative bacterial strain overexpressing a wzz family protein for use as a vaccine antigen either as a conjugate or complexed vaccine. The wzz family protein is preferably wzzB.

In certain preferred embodiments of the invention, the carrier protein is flagellin, optionally selected from the group consisting of flagellin A, flagellin B, phase 1 flagella protein, and phase 2 flagella protein. The flagellin can be from the homologous or a heterologous species as the core-O-polysaccharide hapten.

The invention also encompasses a method of inducing an enhanced immune response in a subject comprising administering to the subject any of the vaccines described herein, preferably in the form of a pharmaceutical composition comprising the vaccine and a pharmaceutically acceptable carrier or adjuvant.

Additional embodiments of the invention also include a kit comprising a package which houses one or more containers which comprises one or more of the vaccines as described herein, instructions for administering the vaccine to a subject, and, optionally, further comprising one or more therapeutic agents.

Furthermore, the embodiments of the invention also encompass a recombinant Gram-negative bacterial strain that constitutively expresses a Wzz family protein and produces increased amounts of long-chain O-polysaccharide for use in conjugate vaccines.

These and other features, aspects, and advantages of the present invention will become better understood with regard to the following description, appended claims, and accompanying figures.

BRIEF DESCRIPTION OF THE DRAWINGS

The following drawings form part of the present specification and are included to further demonstrate certain embodiments of the present invention. The invention may be better understood by reference to one or more of these drawings in combination with the detailed description of specific embodiments presented herein.

FIG. 4A-FIG. 4B are photographs illustrating visualization of LPS produced by *Salmonella enterica* Paratyphi A CVD 1902 overexpressing wzzB. In FIG. 4A, the wzzB gene was expressed in *Salmonella enterica* Paratyphi A from pSE280 plasmid. In FIG. 4B, the wzzB gene was expressed in *Salmonella enterica* Paratyphi A from pSEC10. LPS from whole cells was separated by SDS-PAGE and visualized by staining for polysaccharide. Lane descriptions are indicated; according to an embodiment;

DETAILED DESCRIPTION

Figure 1:
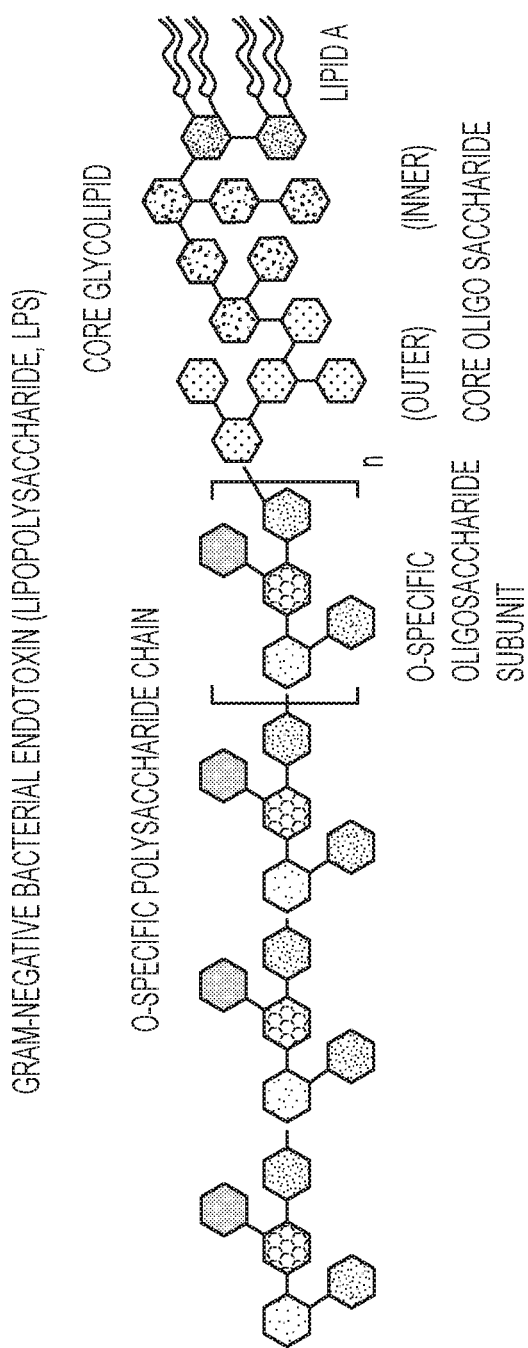
FIG. 1 is a schematic diagram of gram-negative bacterial lipopolysaccharide (LPS)

Surfaces of bacteria mediate a multitude of functions in the environment and in an infected host, including adhesion to both biotic and abiotic substrata, motility, immune system interaction and (or) activation, biofilm formation, and cell-cell communication, with many of these features directly influenced by cell-surface glycans. In Gram-negative bacteria, the majority of cell-surface polysaccharides are produced via the Wzx/Wzy-dependent assembly pathway. The key components of this assembly pathway include the Wzz chain-length regulator proteins, which until recently have resisted detailed structural and functional characterization.

Conjugate vaccines represent among the most complex and expensive vaccines to manufacture, due to several contributing factors. These factors include the need to manufacture the hapten and carrier separately, variability in production of the saccharide hapten which often requires separate sizing steps, and the need to link the saccharide and protein carrier together. Previous attempts to standardize the hapten molecular weight in capsular polysaccharide conjugate vaccines include a sizing step where the large capsule polymer is chemically or mechanically broken down into well-defined and homogenous smaller fragments [4]. A similar strategy has been reported for *Salmonella enterica* serotype *Typhimurium* OPS haptens, whereby a phage-associated endorhamnosidase was used to degrade the O-polysaccharide enzymatically into various modal lengths that were used to establish the minimal immunogenic hapten size [5]. Biochemical size fraction has also been used for *Shigella* OPS, whereby a preferential saccharide size population was established for use in glycoconjugate vaccines [6,7]. In an effort to overcome these drawbacks and produce larger amounts of a more standardized, antigenic, polysaccharide hapten, the invention described herein has used controlled expression of Wzz proteins to bias production of a single saccharide size.

The O-antigen component of the lipopolysaccharide (LPS) is a population of polysaccharide molecules with nonrandom (modal) chain length distribution. The number of the repeat O units in each individual O-antigen polymer (and therefore the length and molecular weight of the polymer chain) depends on the Wzz chain length regulator, an inner membrane protein belonging to the polysaccharide copolymerase (PCP) family. Different Wzz proteins confer vastly different ranges of modal lengths (4 to >100 repeat units), despite having remarkably conserved structural folds. It has been discovered that overexpression of wzz family proteins (e.g., wzzB) in Gram-negative bacteria allows one to manipulate O-polysaccharide length, to shift or bias bacterial production of OPS of certain length ranges, and to enhance production of high-yield large molecular weight lipopolysaccharides containing intermediate or long O-polysaccharides for use as haptens in conjugate vaccines without the need for an additional sizing step.

In the following description, for the purposes of explanation, numerous specific details are set forth in order to provide a thorough understanding of the present invention. It will be apparent, however, to one skilled in the art that the present invention may be practiced without these specific details. In order that the invention may be readily understood and put into practical effect, particular preferred embodiments will now be described by way of the following non-limiting examples.

1. Definitions

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention. Moreover, it should also be understood that as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary. Hence, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount.

Generally, nomenclature used in connection with, and techniques of, cell and tissue culture, molecular biology, immunology, microbiology, genetics, protein, and nucleic acid chemistry and hybridization described herein are those well-known and commonly used in the art. The methods and techniques of the present invention are performed generally according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Science, 4th ed., Eric R. Kandel, James H. Schwartz, Thomas M. Jessell editors. McGraw-Hill/Appleton & Lange: New York, N.Y. (2000). Unless defined otherwise, all technical and scientific terms used herein have the same meaning as commonly understood by one of ordinary skill in the art.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and intended to be non-limiting. Furthermore, where the description of one or more embodiments uses the term "comprising," those skilled in the art would understand that, in some specific instances, the embodiment or embodiments can be alternatively described using the language "consisting essentially of" and/or "consisting of."

The term "manipulating" as used herein means to direct change, or alteration, or a tunable method to control the length of O-polysaccharides by overexpressing wzz family proteins, (e.g., wzzB, wzz, $WZZ_{SF}$, $WZZ_{ST}$, fepE, $WZZ_{fepE}$, wzz1 and wzz2) and/or switching off (i.e., repressing, deleting, removing) wzz family proteins from a Gram-negative bacterial strain.

The term "O-polysaccharide" "OAg" or "O-antigen," as used herein, means a repetitive glycan polysaccharide contained within a lipopolysaccharide (LPS) as shown in FIG.

1. The O-polysaccharide, or OAg, or O-antigen is attached to the core oligosaccharide, and comprises the outermost domain of the LPS molecule. The term "core-O-polysaccharide" as used herein refers to the O-polysaccharide, or Oag, or O-antigen attached to the core oligosaccharide.

The term "subject" as used herein refers to animals, such as mammals. For example, mammals contemplated include humans, primates, dogs, cats, sheep, cattle, goats, pigs, horses, chickens, mice, rats, rabbits, guinea pigs, and the like. The terms "subject", "patient", and "host" are used interchangeably.

The term "hapten" as used herein refers to a small molecule that elicits an immune response only when attached to a large carrier such as a protein.

The term "induce an immune response," as used herein, means inducing a physiological response of the subject's immune system to an immunizing composition. An immune response may include an innate immune response, an adaptive immune response, or both. A protective immune response confers immunological cellular memory upon the subject, with the effect that a secondary exposure to the same or a similar antigen is characterized by one or more of the following characteristics: shorter lag phase than the lag phase resulting from exposure to the selected antigen in the absence of prior exposure to the immunizing composition; production of antibody which continues for a longer period than production of antibody resulting from exposure to the selected antigen in the absence of prior exposure to the immunizing composition; a change in the type and quality of antibody produced in comparison to the type and quality of antibody produced upon exposure to the selected antigen in the absence of prior exposure to the immunizing composition; a shift in class response, with IgG antibodies appearing in higher concentrations and with greater persistence than IgM, than occurs in response to exposure to the selected antigen in the absence of prior exposure to the immunizing composition; an increased average affinity (binding constant) of the antibodies for the antigen in comparison with the average affinity of antibodies for the antigen resulting from exposure to the selected antigen in the absence of prior exposure to the immunizing composition; and/or other characteristics known in the art to characterize a secondary immune response.

The term "modal length" as used herein means number of O polysaccharide repeat units. A "short modal length" as used herein means a low number of repeat units (e.g., 1-15). An "intermediate" or "long" modal length as used herein means a moderate number of repeat units (e.g., 16-50). A "very long modal length" as used herein means >50 O-polysaccharide repeat units.

The term "vaccine," as used herein, means any preparation of biological material containing an antigenic material that upon administration to a subject provides active acquired immunity to at least the pathogenic organism from which the antigenic material was derived. Vaccines can be delivered prophylactically or therapeutically. Conjugate vaccines are used when the antigenic material is poorly immunogenic on its own (such as, for example, polysaccharide antigens), and must be linked to an immunogenic (usually protein) carrier so that it can be recognized more effectively by the immune system. Such poorly immunogenic antigens are termed "haptens." A "hapten," therefore, as used herein, is a small or poorly immunogenic molecule that generally elicits a strong immune response only when attached to a large carrier such as a protein. A "carrier," as used herein, refers to a large molecule, usually a protein, to which a hapten may be attached in a conjugate to produce a vaccine. Carriers can be a molecule that does not elicit an immune response by itself.

The term "wzz family protein," as used herein, means chain length determinant protein of which wzzB, wzz, $wZZ_{SF}$, $WZZ_{ST}$, fepE, $wZZ_{fepE}$, wzz1 and wzz2 are described. The GenBank accession numbers for the wzz gene sequences are AF011910 for E4991/76, AF011911 for F186, AF011912 for M70/1-1, AF011913 for 79/311, AF011914 for Bi7509-41, AF011915 for C664-1992, AF011916 for C258-94, AF011917 for C722-89, and AF011919 for EDL933. The GenBank accession numbers for the G7 and Bi316-41 wzz genes sequences are U39305 and U39306, respectively.

2. Overview

Gram-negative bacteria can cause many types of infections and are spread to humans in a variety of ways. Several species, including *Escherichia coli*, are common causes of food-borne disease and cause the majority of urinary tract infections. *Vibrio cholerae*—the bacteria responsible for cholera—is a waterborne pathogen. Gram-negative bacteria can also cause respiratory infections, such as certain types of pneumonia, and sexually transmitted diseases, including gonorrhea. *Yersinia pestis*, the Gram-negative bacterium responsible for plague, is transmitted to people through the bite of an infected insect or handling an infected animal. *Acinetobacter baumanii* causes disease mainly in healthcare settings. In addition, wound infections caused by *Acinetobacter* have been found in U.S. military personnel who were deployed to Iraq and Afghanistan. *Pseudomonas aeruginosa* causes bloodstream infections and pneumonia in hospitalized patients. It is a common cause of pneumonia in patients with cystic fibrosis. *Klebsiella pneumoniae* causes many types of healthcare-associated infections, including pneumonia, urinary tract infections, and bloodstream infections. *Neisseria gonorrhoeae*, which causes the sexually transmitted disease gonorrhea, is the second most commonly reported infectious disease in the United States.

Gram-negative bacteria are a common source of clinically-relevant bacterial infections that can be established throughout the body. To date, the only major Gram-negative pathogen that is preventable through vaccination is *Haemophilus* influenza type b. Infections by the Gram-negative bacteria that are not currently addressed by any prophylactic therapy cause significant morbidity and mortality, and are associated with large direct and indirect expenses to the healthcare system. Drug-resistant Gram-negative infections, such as *Klebsiella, Pseudomonas*, and *Acinetobacter*, have emerged as major concerns in hospitals, nursing homes and other healthcare settings. In some cases, bacteria can enter the body through urinary and intravenous catheters, ventilators, or wounds and can lead to pneumonia and infections of the bloodstream, bones, joints, and urinary tract. These types of infections disproportionately affect the very ill and the elderly and are often difficult to treat. Therefore, there is a marked interest in the use of O-polysaccharides as the basis of vaccines.

As isolated antigens, O-polysaccharides are poorly immunogenic. Chemical linkage to protein carriers has improved their immunogenicity. However, variability in polymer size represents a practical challenge. In commercial use, the size of the saccharide hapten can influence the compatibility with different conjugation synthesis strategies, product uniformity, and conjugate immunogenicity. Controlling the expression of a Wzz family protein chain length regulator through manipulation of the O-polysaccharide synthesis pathway allows for production of a desired length of O-polysaccharide chains in a variety of Gram-negative bacterial strains.

3. Embodiments

Longer-chain antigenic O-polysaccharide chains for use as a hapten in conjugate vaccines can be produced in a controlled manner using recombinant Gram-negative bacteria that overexpress and/or switch off (e.g., repress, remove, delete) native or heterologous genes of the wzz family, for example wzzB. A preferable length is a length that produces maximal immunogenicity in the context of a given vaccine construct. Bacteria expressing a chosen wzz gene have modified O-polysaccharide chain lengths, allowing the bacteria to produce lipopolysaccharides having the longer O-polysaccharides. The LPS produced by the bacteria can be hydrolyzed to form core-O-polysaccharide molecules that can be conjugated to a carrier molecule, for example flagellin, to produce a vaccine. The invention also provides recombinant bacteria producing the longer chain O-polysaccharides, the polysaccharide molecules, themselves, conjugated vaccines comprising the O-polysaccharides, pharmaceutical compositions and kits.

Recombinant Methods of Manipulating O-Polysaccharide Length to Bias Production of Saccharide Size As illustrated in FIG. 1, LPS is a major component of the outer membrane of Gram-negative bacteria and comprises three domains, or regions: (i) an inner hydrophobic lipid A region (endotoxin), (ii) an oligosaccharide core, and (iii) a an outer O-polysaccharide that is exposed to the bacterial surface and synthesized by a wzz family of proteins. As used herein, the term OPS refers to the outer O-polysaccharide moiety, and COPS refers to the core-O joined polysaccharide, lacking the lipid A region. The O-polysaccharide component of the lipopolysaccharide (LPS) represents a population of polysaccharide molecules with modal chain length distribution. The number of the repeat O units in each individual O-antigen polymer depends on the Wzz chain length regulator, an inner membrane protein belonging to the polysaccharide copolymerase (PCP) family. Different Wzz proteins confer vastly different ranges of modal lengths (4 to >100 repeat units), despite having remarkably conserved structural folds. Gram-negative bacteria often have two different Wzz proteins that confer two distinct OAg modal chain lengths, one longer and one shorter. The Wzz proteins are 36- to 40-kDa inner membrane proteins with substantial variation in sequence identity (~15 to ~80%) but a conserved structural organization.

Methods are provided for manipulating the length of O-polysaccharides produced by a Gram-negative bacterium in culture comprising overexpressing a wzz family protein (e.g., wzzB) from a Gram-negative bacterium in a homologous Gram-negative bacterial strain or in a heterologous Gram-negative bacterial strain to generate a high yield of high molecular weight lipopolysaccharides containing intermediate or long O-polysaccharide chains. A desired chain length is the one which produces maximal immunogenicity in the context of a given vaccine construct. In other embodiments, methods are provided for overexpressing a wzz family protein (e.g., wzzB) from a Gram-negative bacterium in a homologous Gram-negative bacterial strain or in a heterologous Gram-negative bacterial strain and/or switching off (i.e., repressing, deleting, removing) a second wzz gene (e.g., wzzB) to generate a high yield of high molecular weight lipopolysaccharides containing intermediate or long O-polysaccharide chains. For example, overexpress wzz2 but also switch off wzz1. Or, in the alternative, overexpress wzzfepE and switch off wzzB. In another embodiment, it may be preferable to overexpress wzzB but switch off wzzfepE.

The Gram-negative bacterium preferably is selected from the group consisting of Acinetobacter, Burkholderia, Bordetella, Campylobacter, Escherichia coli, Francisella, Haemophilus, Helicobacter, Pseudomonas, Salmonella enterica, Shigella, Vibrio, and Yersinia species. More preferably, the Gram-negative bacterial strain is selected from the group consisting of *Salmonella enterica* serotype *Enteritidis* CVD 1943, *Salmonella enterica* serotype *Typhimurium* CVD 1925, *Salmonella enterica* serotype Paratyphi A CVD 1902, and *Shigella flexneri* CVD 1208S.

Representative bacterial strains are set forth in Table 1. Gram-negative bacterial strains in preferred embodiments are selected from the group consisting of *Salmonella Enteritidis* CVD 1943, *Salmonella Typhimurium* CVD 1925, *Salmonella* Paratyphi A CVD 1902, *Salmonella* Newport CVD 1962, and *Shigella flexneri* CVD 1280S. A description of the generation of these bacterial strains sequences is found in U.S. Patent Application Pub. No. 2013/0129776 A1, which is hereby incorporated by reference.

TABLE 1

Representative Bacterial Strains and Plasmids

| Bacteria and plasmids | Genotype | Characteristics | Reference |
| --- | --- | --- | --- |
| Bacterial strains | | | |
| *Salmonella enterica* serovar Enteritidis CVD 1943 | ΔguaBA ΔclpP ΔfliD | Reagent strain for conjugate vaccine production | Tennant et al Infect Immun 2011 79: 4175-85 |
| *Salmonella enterica* serovar Typhimurium CVD 1925 | ΔguaBA ΔclpP ΔfliD ΔfljB | Reagent strain for conjugate vaccine production | Tennant et al Infect Immun 2011 79: 4175-85 |
| *Salmonella enterica* serovar Paratyphi A CVD 1902 | ΔguaBA ΔclpX | Candidate live attenuated vaccine | |
| *Shigella flexneri* CVD 1208S | ΔguaBA Δset Δsen | Candidate live attenuated vaccine | Kotloff et al 2007 (Human Vaccines 3: 628-275) |
| *Salmonella enterica* serovar Newport CVD 1962 | ΔguaBA ΔclpX | Reagent strain for conjugate vaccine production | |
| *Pseudomonas aeruginosa* PAO1 | | Wild-type | |
| *Pseudomonas aeruginosa* PAK | | Wild-type | |

TABLE 1-continued

Representative Bacterial Strains and Plasmids

| Bacteria and plasmids | Genotype | Characteristics | Reference |
| --- | --- | --- | --- |
| *Pseudomonas aeruginosa* O1 | | Wild-type | |
| *Pseudomonas aeruginosa* O2 | | Wild-type | |
| *Pseudomonas aeruginosa* O3 | | Wild-type | |
| *Pseudomonas aeruginosa* O4 | | Wild-type | |
| *Pseudomonas aeruginosa* O6 | | Wild-type | |
| *Pseudomonas aeruginosa* O10 | | Wild-type | |
| *Pseudomonas aeruginosa* O11 | | Wild-type | |
| *Pseudomonas aeruginosa* O12 | | Wild-type | |
| Plasmids | | | |
| pSEC10 | | 7.2 kb, low copy number, Kan resistant | Stokes et al. 2007. Infection and Immunity. 75(4): 1827-34 |
| pSE280 | | 3.9 kb, high copy number, Amp resistant | |
| pUCP19 | | 5.9 kb, high copy number, Amp resistant | Schweizer Gene 1991 97: 109-21 |

The Wzy Pathway

Synthesis of bacterial polysaccharides via the Wzx/Wzy-dependent pathway is described in Islam and Lam, Can. J. Microbiol. 60: 697-716 2015, pp. 697-716 which is incorporated herein by reference. The role of wzz was first identified via the loss of preferred O-polysaccharide chain modalities in mutants, leading to initial gene names such as regulator of O-chain length (rol) (Batchelor et al. 1991) or chain length determinant (cld) (Bastin et al. 1993). These PCP proteins can be readily identified via standard BLASTp searches. Also, wzz position within the chromosome of a particular species is often conserved. For example, in *Pseudomonas aeruginosa*, wzz1 is the next gene downstream of himD in all 20 serotypes (Raymond et al. 2002).

The modal number of O-polysaccharide polymer repeats for Gram-negative bacteria using the Wzy LPS synthesis system is controlled by Wzz proteins. The protein structure and specificity of Wzz family members varies between bacterial species. Table 3 illustrates wzz genes in representative bacterial strains. Some bacteria encode several different wzz genes (e.g., *Salmonella Typhimurium* and *Salmonella flexneri*). Their expression can be subject to control by growth phase and environmental conditions. Controlled expression of Wzz proteins can be used to bias production of a single saccharide size. Manipulation of the O-polysaccharide synthesis pathway represents an efficient and economical approach to achieve high yields of these O-polysaccharide size populations, as this approach enables enhanced expression and minimal requirements for additional later process steps.

TABLE 2 wzz genes in Representative Bacterial Strains

| Gram-negative Bacterium | wzz gene | Modal Length |
| --- | --- | --- |
| *Escherichia coli* | wzzK12 GenBank: AAC75088 | Short/medium: <16 repeat units |
| *Salmonella enterica* ser. Enteritidis | wzzB GenBank: AM933172.1 | Long: 16 to 35 repeat units |
| | wzzBfepE GenBank: CP007468.1 | Very Long: >100 repeat units |
| *Salmonella enterica* ser. Typhimurium | wzzST GenBank: Z17278.1 | Long: 16 to 35 repeat units |
| | wzzFepE NCBI Reference Sequence: NC_003197.1 | Very Long: >100 repeat units |
| *Salmonella enterica* ser. Paratyphi A | wzzB GenBank: CP011967.1 | Short/medium: <16 repeat units |
| *Salmonella enterica* ser. Newport | wzzB GenBank: CP007216.1 | Long: 16 to 35 repeat units |
| | wzzBfepE GenBank: CP007216.1 | Very Long: >100 repeat units |
| *Shigella flexneri* | wzzSF GenBank: X71970.1 | Intermediate: 11-17 repeat units |
| | $wzz_{pHS-2}$ | Very Long: 90-100 repeat units |
| *Salmonella enterica* ser. Typhi | wzzSTY GenBank: CAD02441 | Long: 16 to 35 repeat units |
| *Pseudomonas aeruginosa* | wzz1 GenBank: AE004091.2 | Long: 20 to 50 repeat units |
| *Pseudomonas aeruginosa* | wzz2 GenBank: AE004091.2 | Very Long: >100 repeat units |

TABLE 2-continued wzz genes in Representative Bacterial Strains

| Gram-negative Bacterium | wzz gene | Modal Length |
| --- | --- | --- |
| Vibrio cholerae | $wzz_{O139}$ GenBank: X90547.1 | Short: 1 repeat unit |
| Yersinia pestis | wzzYP GenBank: CAC92336 | |

In *Salmonella enterica* serovar *Typhimurium*, we observed that despite encoding a Wzz protein that specifies intermediate modal length O-polysaccharide, the LPS is primarily short with the intermediate molecular weight population poorly expressed under normal growth conditions. In certain embodiments, overexpression of the intermediate O-polysaccharide modal length wzz gene from a plasmid overcame this deficiency, resulting in the production of ~10-fold higher levels of the desired saccharide size.

*Salmonella enterica* serovar Paratyphi A is a serogroup A *Salmonella* producing OPS that are structurally very similar to *Salmonella enterica* serovar *Typhimurium* [8], and express almost entirely short-chain OPS. In certain embodiments of this invention, overexpression of wzzB from *Salmonella enterica* serovar *Typhimurium* in *Salmonella enterica* serovar Paratyphi A shifted the saccharide population to intermediate length LPS. *Shigella flexneri* 2a expresses separate chromosomally- and plasmid-encoded wzz genes that specify either short or very-long LPS types [9]. These wzz genes are discordantly regulated, and neither produces the modal length specified by *Salmonella enterica* serovar *Typhimurium* wzzB. High level expression of wzzB from *Salmonella enterica* serovar *Typhimurium* in *Shigella flexneri* supplanted almost fully the action of the endogenously encoded Wzz proteins, producing a homogenous population of relatively intermediate molecular weight LPS. This discovery as further described herein provides precedent for shifting the saccharide size from both long and short towards an intermediate and uniform size.

Plasmids as a Tool for Overexpression of Wzz Family of Proteins

Vector DNA can be introduced into host organisms by transformation. Some vectors not only allow the isolation an dpurificaiton of a particular DNA but also drive the expression of genes within the insert DNA. These plasmids are called expression vectors and have transcriptional promoters, derived from the host cell, immediately adjacent to the site of insertion. Expression vectors, or expression constructs, are usually a plasmid or virus designed for gene expression in cells. Representative plasmids are described in Table 1.

If the coding region of a gene (without its promoter) is placed at the site of insertion in the proper orientation, then the inserted gene will be transcribed into mRNA and translated into protein by the host cell. The vector is used to introduce a specific gene into a target cell, and can commandeer the cell's mechanism for protein synthesis to produce the protein encoded by the gene. Expression vectors are the basic tools in biotechnology for the production of proteins. The plasmid is engineered to contain regulatory sequences that act as enhancer and promoter regions and lead to efficient transcription of the gene carried on the expression vector. The goal of a well-designed expression vector is the efficient production of protein, and this may be achieved by the production of significant amount of stable messenger RNA, which can then be translated into protein. The expression of protein may be tightly controlled and protein is only produced in significant quantity when necessary through the use of an inducer, in some systems however the protein may be expressed constitutively. *Escherichia coli* is commonly used as the host for protein production, but other cell types may also be used.

An expression vector must have elements necessary for gene expression. These may include a strong promoter, the correct translation initiation sequence such as a ribosomal binding site and start codon, a strong termination codon, and a transcription termination sequence. There are differences in the machinery for protein synthesis between prokaryotes and eukaryotes, therefore the expression vectors must have the elements for expression that is appropriate for the chosen host. For example, prokaryotes expression vectors would have a Shine-Dalgarno sequence at its translation initiation site for the binding of ribosomes, while eukaryotes expression vectors would contain the Kozak consensus sequence The promoter initiates the transcription and is therefore the point of control for the expression of the cloned gene. The promoters used in expression vector are normally inducible, meaning that protein synthesis is only initiated when required by the introduction of an inducer such as IPTG. Gene expression however may also be constitutive (i.e. protein is constantly expressed) in some expression vectors. Low level of constitutive protein synthesis may occur even in expression vectors with tightly controlled promoters.

Figure 2:
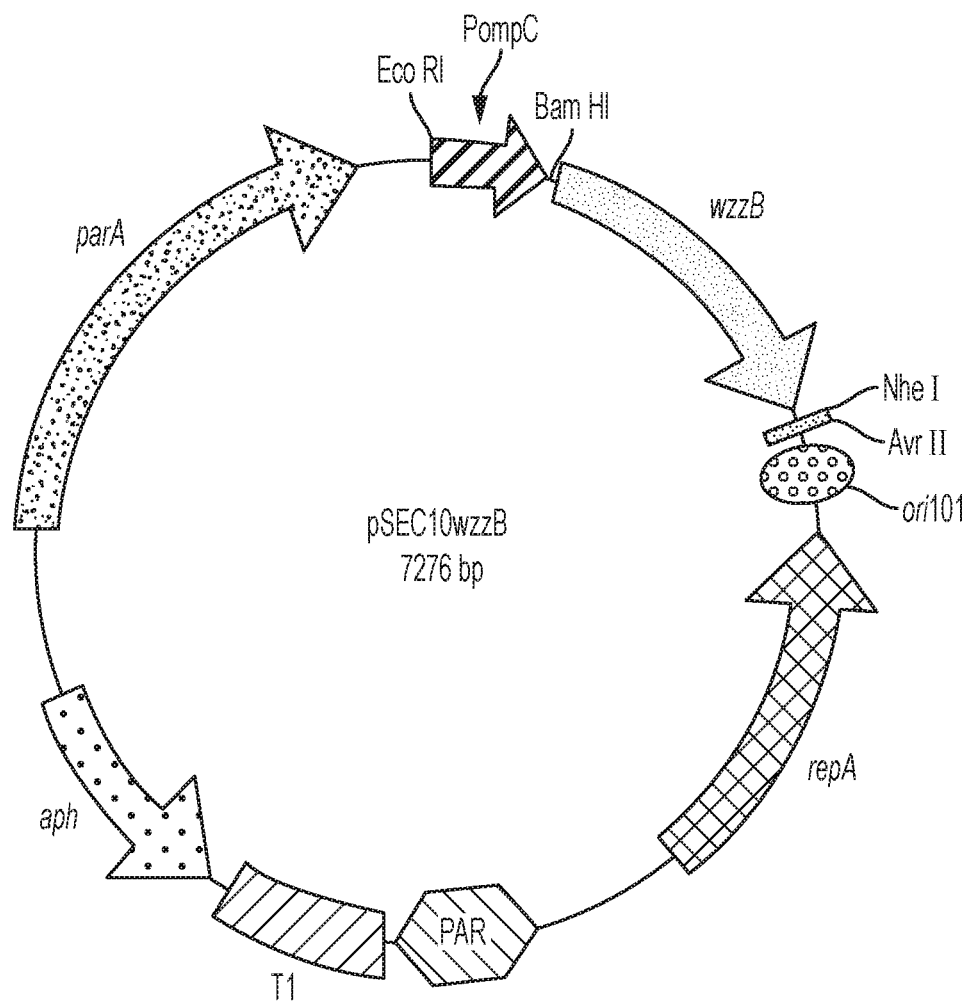
FIG. 2 is a schematic diagram of a pSEC10-wzzB expression plasmid. The *Salmonella enterica* serotype *Typhimurium* wzzB gene was cloned downstream of PompC in the highly stable, kanamycin-resistant plasmid, pSEC10; according to an embodiment.

A 7275-base pair-plasmid pSEC10-wzzB is provided in certain embodiments described herein (FIG. 2). pSEC10-wzzB is a non-transmissible low copy number expression plasmid which encodes resistance to the antibiotic kanamycin. pSEC10-wzzB carries the 984-bp-gene wzzB that encodes a 36.3 kDa (327 amino acid) WzzB protein that controls O-polysaccharide chain length. Overexpression of a wzz family protein (e.g., wzzB) may occur from a high copy number plasmid (i.e., pSE280, pUCP19) or from a low copy plasmid (i.e., pSEC10) in certain embodiments. In other embodiments, overexpression of a wzz gene (e.g., wzzB or any wzzB homolog) may occur from the chromosome. In such cases, the endogenous wzz gene is or is not deleted. Methods for site-specific insertion of transgenes into chromosomes are described in McKenzie and Craig, "Fast, easy and efficient: site-specific insertion of transgenes into Enterobacterial chromosomes using Tn7 without need for selection of the insertion event," BMC Microbiology 2006, 6: 39 pp.1-7. For example, the wzzB gene may first be cloned into a high copy number, ampicillin-resistant plasmid pSE280. wzzB is amplified from S. *Typhimurium* 177 using primers. The 1 kb-PCR product was purified and then digested with BamHI and PstI. The digested product was ligated to similarly digest pSE280 and electroporated into *E. coli* DH5alpha. pSE280-wzzB plasmid DNA was isolated and the plasmid was subsequently electroporated into bacterial strains of interest. In other embodiments, wzzB was cloned from pSE280-wzzB into pSEC10, a non-transmissible low copy number expression plasmid which encodes resistance to kanamycin. A 984-bp-fragment encoding wzzB was inserted as a BamHI-NheI fragment into pSEC10 cleaved with BamHI and NheI. The resultant plasmid pSEC10-wzzB is 7275 base pairs (bp).

In summary, it has been discovered that overexpression of different Wzz proteins (e.g., WzzB) allows for a tunable method for control of oligosaccharide size. This approach as described herein may be used to generate OPS haptens for several important GNB pathogens that use the Wzy system (e.g., *Acinetobacter, Burkholderia, Bordetella, Campylobacter, Escherichia coli, Francisella, Haemophilus, Helicobacter, Pseudomonas, Salmonella enterica, Shigella, Vibrio,* and *Yersinia* species.) More preferably, the Gram-negative bacterial strain is selected from the group consisting of *Salmonella enterica* serotype *Enteritidis* CVD 1943, *Salmonella enterica* serotype *Typhimurium* CVD 1925, *Salmonella enterica* serotype Paratyphi A CVD 1902, and *Shigella flexneri* CVD 1208S. This novel genetic approach towards vaccine hapten production provides an important advance towards enabling efficient production of O-polysaccharide and core-O-polysaccharide molecules as vaccine components.

Recombinant Gram-Negative Bacterial Strains Overexpressing Wzz Family Proteins

Recombinant Gram-negative bacterial strains that constitutively express a Wzz family protein and produce increased amounts of long-chain O-polysaccharide for use in conjugates are provided. Preferable Gram-negative bacterial strains are provided and discussed in the Examples herein. It is desirable to have any Gram-negative bacterial strain that overexpresses a Wzz family protein (e.g., *Acinetobacter, Burkholderia, Bordetella, Campylobacter, Escherichia coli, Francisella, Haemophilus, Helicobacter, Pseudomonas, Salmonella, Shigella, Vibrio,* and *Yersinia*). In certain embodiments, overexpression of wzzB from *Salmonella Typhimurium* CVD 1925 (177 ΔguaBA ΔclpP ΔfliD ΔfljB) creates a shift towards the intermediate (long) LPS phenotype, with approximately tenfold more long-chain LPS produced relative to CVD 1925 without plasmid, or containing the empty plasmid vector. Comparable results were found when wzzB was expressed from high-copy (pSE280) and low-copy (pSEC10) plasmids. In other embodiments, plasmids expressing wzzB from *Salmonella enterica* serotype *Typhimurium* were used to transform a heterologous *Salmonella* serovar (*Salmonella enterica* serotype Paratyphi A), as well as a heterologous bacterial species (*Shigella flexneri* 2a). When the *Salmonella enterica* serotype *Typhimurium* wzzB was expressed in *Salmonella enterica* serotype Paratyphi A, the O-polysaccharide produced was similarly shifted almost entirely from low-molecular weight to a long modal length. When wzzB from *Salmonella enterica* serotype *Typhimurium* was expressed in *Shigella flexneri* 2a CVD 1208S, a modal shift was seen from short and very long repeat containing OPS, to a uniform high molecular weight species that was intermediate between the short and very long O-polysaccharide length.

Lipopolysaccharides Isolated from Gram-Negative Bacterial Strains Overexpressing Wzz Proteins In certain embodiments, lipopolysaccharides from Gram-negative bacteria (e.g., *Salmonella Typhimurium*) overexpressing a Wzz family protein in Gram-negative bacterial strains including but not limited to those in Table 1 are provided. Overexpression of a wzz family protein may shift lipopolysaccharides from one modal length to another. For example, those lipopolysaccharides containing intermediate chain length O-polysaccharides may shift to lipopolysaccharides containing long chain length O-polysaccharides. For example, in certain embodiments, overexpression of wzzB from *Salmonella Typhimurium* CVD 1925 generates a shift from a low number of O-polysaccharide repeat units toward the intermediate (long) lipopolysaccharide. In other embodiments, plasmids expressing a wzz family protein (e.g., wzzB) can be used to transform a heterologous *Salmonella* serovar (i.e., *Salmonella* Paratyphi A), as well as a heterologous bacterial species (*Shigella flexneri* 2a). In certain embodiments, when expression of *Salmonella Typhimurium* wzz family protein (e.g., wzzB) is expressed in *Salmonella* Paratyphi A, the O-polysaccharide produced similarly shifts almost entirely from a low-molecular weight to a long modal length. In other embodiments, when a wzz family protein (e.g., wzzB) was expressed in *Salmonella flexneri* 2a CVD 1208S, a modal shift was seen from short and very long repeat containing O-polysaccharides, to a uniform high molecular weight species that was intermediate between the short and very long O-polysaccharide chain length. A high yield of large molecular weight lipopolysaccharides containing intermediate or long O-polysaccharides is preferred. A desired chain length is the one which produces maximal immunogenicity in the context of a given vaccine construct.

The main problem with LPS purification protocols that is common in the art is the contamination of the end product with nucleic acids and proteins in variable proportions which could potentially interfere with other applications. In order to eliminate contaminating protein and nucleic acids, those of skill in the art have found that treatment with proteinase K, DNase and RNase prior to extraction step yields a pure product. Isolated LPS samples can be electrophoresed on 15% SDS-polyacrylamide gels for 13 to 14 hours at 12 mA. Purity of extracted LPS may be evaluated by silver staining of SDS-PAGE gels and HPLC analysis. The genes may be stained with silver nitrate and developed with formaldehyde. Sliver staining is a highly sensitive method capable of detecting as low as 1 ng LPS and is routinely used for visualization of the band pattern of purified LPS.

Core-O-Polysaccharide Purification

Purification can be employed to remove unreacted polysaccharide, protein, or small molecule reaction byproducts. Purification methods include ultrafiltration, size exclusion chromatography, density gradient centrifugation, hydrophobic interaction chromatography, ammonium sulfate fractionation, ion exchange chromatography, ligand exchange chromatography, immuno-affinity chromatography, polymyxin-b chromatography, and the like, as are known in the art. In some embodiments, the conjugation reactions proceed with higher yield, and generate fewer undesirable small molecule reaction byproducts. Accordingly, in some embodiments no purification may be necessary, or only a minor degree of purification can be desirable.

Methods of purification of core-O-polysaccharides from LPS are known in the art. After purification of LPS, purified LPS may be hydrolyzed by heating in 1% (v/v) acetic acid for 90 minutes at 100 degrees Celsius, followed by ultracentrifugation at 142,000×g for 5 hours at 4 degrees Celsius. The supernatant containing the core-O-polysaccharide is freeze-dried and stored at 4 degrees Celsius. In certain embodiments, deletion of capsule synthesis genes to enable simple purification of core-O-polysaccharide is described. For example, purification of core-O-polysaccharide from *Salmonella Enteritidis* CVD 1943 ΔguaBA ΔclpPX ΔfliD fermentation culture includes the steps of: (i) OPS extraction via 1% HOAc/100 degrees Celsius; (iii) removal of bacteria, insoluble lipid A and precipitated protein with centrifugation and filtration; (iv) concentrate and remove low molecular weight contaminants by tangential flow filtration; (v) remove free lipid A, nucleic acid and protein by anion exchange chromatography; (vi) remove protein in ammonium sulfate precipitation; (vii) concentrate and buffer exchange with tangential flow filtration.

The core-O-polysaccharide hapten can be isolated by methods including, but not limited to mild acid hydrolysis to remove lipid A from LPS. Other embodiments may include use of hydrazine as an agent for COPS preparation. Preparation of LPS can be accomplished by known methods in the art. In some embodiments, LPS is prepared according to methods of Darveau et al. J. Bacteriol., 155(2):831-838 (1983), or Westphal et al. Methods in Carbohydrate Chemistry. 5:83-91 (1965) which are incorporated by reference herein. LPS may be purified by a modification of the methods of Darveau et al., supra, followed by mild acid hydrolysis to remove lipid A.

In certain embodiments, core-O-polysaccharides purified from wild-type, modified, or attenuated Gram-negative bacterial strains including but limited to those described in Table 1 (e.g., *Salmonella Typhimurium* CVD 1925, *Salmonella* Paratyphi A CVD 1902, and *Shigella flexneri* CVD 1208S) that overexpress a Wzz family protein (e.g., wzzB) are provided for use as haptens in conjugate vaccines. In preferred embodiments, the core-O-polysaccharide chain is purified from the Gram-negative bacterial strain overexpressing wzz protein for use as a vaccine antigen either as a conjugate or complexed vaccine.

O-Polysaccharide Purification

Purification methods are known in the art that maximize recovery of O-polysaccharides are known in the art and are described in Kim, et al., "Purification of O-specific polysaccharide from lipopolysaccharide produced by *Salmonella enterica* serovar Paratyphi A," *Vaccine*. 2014 May 1; 32(21): 2457-62. Epub 2014 Mar. 12. After fermentation, bacterial cells are concentrated and washed, the permeate containing the free LPS processed separately from the cells. The free LPS is then concentrated and washed on a 100 kD ultrafiltration membrane to remove low molecular weight impurities. The LPS is detoxified by separation of the lipid A from the O-polysaccharide using acid hydrolysis at 100° C., the precipitated lipid A was removed by 0.2 m membrane filtration. Contaminants were then removed by acid precipitation in the presence of sodium deoxycholate. The O-polysaccharide was then concentrated and washed with 1M NaCl then water using a 10 kD ultrafiltration membrane then sterile filtered through a 0.2 m membrane filter. The cells were treated by acid hydrolysis at 100° C., the remaining cells, cell debris and precipitate was removed by centrifugation. The filtrate is then treated in the same way as described above for the free LPS. O-polysaccharide chains purified from a Gram-negative bacterial strain overexpressing a wzz family protein for use as a vaccine antigen either as a conjugate or complexed vaccine are provided. In certain embodiments, the wzz family protein is wzzB.

Carrier Proteins

Conjugate or complexed vaccines in certain embodiments may contain the core-O-polysaccharide hapten covalently linked or complexed to a carrier protein as described in Table 4, which is intended to be non-limiting. In preferred embodiments, the carrier protein is a flagellin molecule.

TABLE 4

Representative Examples of Carrier Proteins
Carrier Protein

Flagellin A
Flagellin B
Phase 1 flagella protein
Phase 2 flagella protein
Diptheria toxin or toxoid
Genetically detoxified Diphtheria toxins Cross-reacting material 197 (CRM197)
Tetanus toxin or toxoid
*Pseudomonas* exotoxin A
Cholera toxin or toxoid
Group A streptococcal toxins
Pneumolysin of *Streptococcus pnneumoniae*
Pneumococcal surface protein A (PSPA) of *Streptococcus pneumoniae*
Flimantous haemagglutinin (FHA)
FHA fragments of *Bordetella pertussis*
pili or pilins of *Neisseria gonorrhoeae*
pili or pilins of *Neisseria meningitidis*
outer membrane proteins of *Neisseria meningitidis*,
outer membrane proteins of *Neisseria gonorrhoeae*
C5A peptidase of *Streptococcus* and surface protein of *Moraxella catarrhalis*.
Recombinant exoprotein A of *Pseudomonas aeruginosa* (rEPA)
*Haemophilus influenzae* protein D Core-O-polysaccharides and carrier proteins can be conjugated using known techniques and methods. Certain embodiments are provided where the core-O-polysaccharide and the carrier protein are chemically conjugated or complexed using a cross-linker or polymer. The carrier protein may be from a homologous bacterial strain or a heterologous bacterial strain. For example, techniques to conjugate the core-O-polysaccharide and the Phase 1 flagella protein can include, in part, coupling through available functional groups (such as amino, carboxyl, thio and aldehyde groups). See, e.g., Hermanson, Bioconjugate Techniques (Academic Press; 1992); Aslam and Dent, eds. Bioconjugation: Protein coupling Techniques for the Biomedical Sciences (MacMillan: 1998); S. S. Wong, Chemistry of Protein Conjugate and Crosslinking CRC Press (1991); and Brenkeley et al., Brief Survey of Methods for Preparing Protein Conjugates With Dyes, Haptens and Cross-Linking Agents, Bioconjugate Chemistry 3:1 (January 1992).

The core-O-polysaccharide hapten and carrier of the conjugate can be chemically conjugated using conventional crosslinking agents such as carbodiimides. Examples of conjugation chemistry used to achieve efficient synthesis of the hapten-carrier conjugates are disclosed in Lees, A. et al. 1996, Vaccine 14(3):190-198, and Shafer, D E et al. 2000, Vaccine 18(13):1273-81; which are incorporated by reference herein. Linkers and coupling reagents known to those of ordinary skill in the art are also suitable for use. Such compounds are discussed in detail by Dick et al., Conjugate Vaccines, J. M. Cruse and R. E. Lewis, Jr., eds., Karger, New York, pp. 48-114, hereby incorporated by reference.

Conjugation may be conducted at a temperature of from about 0° Celsius to about 5° Celsius for about 36 to about 48 hours. In one embodiment, conjugation is conducted at about 4° Celsius for about 36 hours, followed by about an additional 18 to 24 hours at a temperature of from about 20° Celsius to about 25° Celsius. In another embodiment, conjugation is conducted for about 18 hours at about 20° to 240 Celsius such that the residual cyanate groups react with water and decompose. Longer or shorter conjugation times and/or higher or lower conjugation temperatures can be employed, as desired. In some embodiments, it is desirable, however, to conduct the conjugation reaction, at least initially, at low temperatures, for example, from about 0° Celsius to about 5° Celsius, such as about 4° Celsius, so as to reduce the degree of precipitation of the conjugate.

Pharmaceutical Compositions

In some embodiments, the conjugate or complexed vaccine is administered to a subject as a pharmaceutical composition. This pharmaceutical composition may contain salts, buffers, adjuvants, or other compounds that are desirable for improvement of efficacy. In some embodiments, adjuvants are used in an effort to induce or improve a specific immune response. Descriptions of adjuvants are described in Warren et al. (Ann. Rev. Biochem., 4:369-388, 1986), the entire disclosure of which is hereby incorporated by reference. Examples of materials suitable for use in conjugate vaccine compositions are known to those of skill in the art and are described in Remington's Pharmaceutical Sciences (Osol, A, Ed, Mack Publishing Co, Easton, Pa., pp. 1324-1341 (1980), which disclosure is incorporated herein by reference).

In some embodiments, the conjugate vaccine can be formulated into liquid gaseous, or solid preparations (including tablets and capsules, solutions, suspensions, emulsions, vapors, powders, and the like) for, e.g., nasal, rectal, buccal, vaginal, peroral, intragastric, mucosal, perlinqual, alveolar, gingival, olfactory, or respiratory mucosa administration. Suitable forms for such administration include solutions, suspensions, emulsions, syrups, and elixirs. The conjugate vaccines can also be formulated for parenteral, subcutaneous, intradermal, intramuscular, intraperitoneal or intravenous administration, injectable administration, sustained release from implants, or administration by eye drops. Suitable forms for such administration include sterile suspensions and emulsions. Such conjugate vaccines can be in admixture with a suitable carrier, diluent, or excipient such as sterile water, physiological saline, glucose, and the like. The conjugate vaccines can also be lyophilized. The conjugate vaccines can contain auxiliary substances such as wetting or emulsifying agents, pH buffering agents, gelling or viscosity enhancing additives, preservatives, flavoring agents, colors, fillers, and the like, depending upon the route of administration and the preparation desired A person of ordinary skill in the art may prepare suitable preparations consulting references such as Remington: The Science and Practice of Pharmacy (22nd edition, 2012; 21st edition, 2005), Pharmaceutical Press; Remington: The Science and Practice of Pharmacy (20th edition, 2003; 19th edition, 1995), Lippincott Williams & Wilkins; and Remington's Pharmaceutical Sciences (18th edition, 1990), Mack Printing Co.; which are incorporated herein by reference in their entirety.

Administration

In some embodiments, the conjugate vaccine is administered parenterally. Parenteral vehicles include sodium chloride solution, Ringer's dextrose, dextrose and sodium chloride, lactated Ringer's or fixed oils and other vehicle known to one of skill in the art. Intravenous vehicles may include fluid and nutrient replenishers, electrolyte replenishers (such as those based on Ringer's dextrose). In some embodiments, the conjugate vaccines for parenteral administration may be in the form of a sterile injectable preparation, such as a sterile injectable aqueous or nonaqueous solutions, suspensions, and emulsions. Examples of nonaqueous solvents are propylene glycol, polyethylene glycol, vegetable oils such as olive oil, and injectable organic esters such as ethyl oleate. Carriers or occlusive dressings can be used to increase skin permeability and enhance antigen absorption. Suspensions may be formulated according to methods well known in the art using suitable dispersing or wetting agents and suspending agents. The sterile injectable preparation may also be a sterile injectable solution or suspension in a parenterally acceptable diluent or solvent, such as a solution in 1, 3-butanediol. Suitable diluents include, for example, water, Ringer's solution and isotonic sodium chloride solution. In addition, sterile fixed oils may be employed conventionally as a solvent or suspending medium. For this purpose, any bland fixed oil may be employed including synthetic mono- or diglycerides. In addition, fatty acids such as oleic acid may likewise be used in the preparation of injectable preparations.

Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

In some embodiments, the conjugate vaccine is provided as a liquid suspension or as a freeze-dried product. Suitable liquid preparations include, e.g., isotonic aqueous solutions, suspensions, emulsions, or viscous compositions that are buffered to a selected pH. Transdermal preparations include lotions, gels, sprays, ointments or other suitable techniques. If nasal or respiratory (mucosal) administration is desired (e.g., aerosol inhalation or insufflation), compositions can be in a form and dispensed by a squeeze spray dispenser, pump dispenser or aerosol dispenser. Aerosols are usually under pressure by means of a hydrocarbon. Pump dispensers can preferably dispense a metered dose or a dose having a particular particle size, as discussed below.

In certain embodiments, the conjugate vaccine may be provided in the form of a solution, suspension and gel. In other embodiments, formulation of the conjugate vaccine may contain a major amount of water that may be purified in addition to the active ingredient. Minor amounts of other ingredients such as pH adjusters, emulsifiers, dispersing agents, buffering agents, preservatives, wetting agents, jelling agents, colors, and the like can also be present.

Pharmaceutical compositions may be administered in a number of ways either alone or in combination with other treatments, either simultaneously or sequentially depending on the condition to be treated and whether local or systemic treatment is desired. Administration may be by direct injection, or by intrathecal injection, or intravenously, or by stereotaxic injection. The route of administration can be selected based on the disease or condition, the effect desired, and the nature of the cells being used. Actual methods of preparing dosage forms are known, or will be apparent, to those skilled in the art. (See Remington: The Science and Practice of Pharmacy, 22nd edition, 2012, Pharmaceutical Press.) Where a composition as described herein is to be administered to an individual, administration is preferably in a "prophylactically effective amount" or a "therapeutically effective amount," this being sufficient to show benefit to the individual.

The number of administrations can vary. Alternatively, administration may be, for example, daily, weekly, or monthly. The actual amount administered, and rate and time-course of administration, will depend on the age, sex, weight, of the subject, the stage of the disease, and severity of what is being treated (including prophylactic treatment).

Prescription of treatment, e.g., decisions on dosage is within the responsibility of general practitioners and other medical doctors.

Kits

In some embodiments, kits comprise one or more vaccines of the invention. The materials described herein as well as other materials can be packaged together in any suitable combination as a kit useful for performing, or aiding in the performance of, the disclosed method. It is useful if the kit components in a given kit are designed and adapted for use together in the disclosed method.

In some embodiments, the kit is a package which houses one or more containers that comprises one or more pharmaceutical compositions. The pharmaceutical compositions may be placed within containers, or kits, along with packaging material which provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition. In some embodiments, the kit may comprise one or more therapeutic agents or diagnostic tool.

In some embodiments, the kit may comprise a schedule for immunization of the pharmaceutical composition. In some embodiments, a cocktail containing two or more conjugate vaccines can be included, or separate pharmaceutical compositions containing different conjugate vaccines or therapeutic agents. The kit may contain separate doses of the conjugate vaccine for serial or sequential administration. The kit also can comprise one or more pharmaceutical compositions comprising the attenuated bacterial strains as described herein for use as a conjugate vaccine, or for use as a vaccine as a prime or boost in conjunction with a conjugate vaccine described herein.

In some embodiments, the kit further comprises a device or devices suitable for delivery. For example, the kit may further comprise syringes another device (e.g., inhaler) for administration of the conjugate vaccine or other therapeutic agents with instructions for administration, storage, reconstitution, and administration of any or all conjugate vaccine or other therapeutic agents included. A plurality of containers reflecting the number of administrations to the subject may be included.

Methods of Enhancing Immune Response

Methods are provided for inducing an immune response in a subject comprising administering to a subject a conjugate vaccine or complexed vaccine comprising a core-O-polysaccharide hapten covalently linked or complexed to a carrier protein in an amount sufficient to induce an immune response in the subject. All strains do not have to be administered within the same inoculum, but may be divided into separate doses administered on sequential days to achieve complete coverage.

In some embodiments, methods are provided for inducing an immune response, comprising administering to a subject in need thereof an immunologically-effective amount of a conjugate *Salmonella enterica* serovar *Typhimurium* vaccine, comprising conjugates from bacterial strains described herein overexpressing wZZ (e.g., wzzB) and/or repressing wZZ, wherein the conjugates comprise a core-O-polysaccharide hapten and a carrier antigen, wherein at least one of the hapten antigens or carrier antigens is from the *Salmonella enterica* serovar *Typhimurium* overexpressing wzz (e.g., wzzB). In some embodiments, the hapten antigen is a core-O-polysaccharide (COPS) from the *Salmonella enterica* serovar *Typhimurium* overexpressing wZZ and the carrier is a phase 1 flagella protein (FliC) or an antigenic fragment or derivative thereof from the *Salmonella enterica* serovar *Typhimurium.*

Immunogenicity of the conjugates of the invention is greater than the immunogenicity of at least one of the carriers alone. Methods of measuring immunogenicity are well known to those in the art and primarily include measurement of serum antibody including measurement of amount, avidity, and isotype distribution at various times after injection of the conjugate vaccine. Greater immunogenicity may be reflected by a higher titer and/or increased life span of the antibodies. Immunogenicity may also be measured by the ability to induce protection to challenge with noxious substances or virulent organisms. Immunogenicity may also be measured by the ability to immunize neonatal and/or immune deficient mice. Immunogenicity may be measured in the patient population to be treated or in a population that mimics the immune response of the patient population.

The conjugate vaccine is administered alone in a single dose or administered in sequential doses. In other embodiments, the conjugate vaccine is administered as a component of a homologous or heterologous prime/boost regimen in conjunction with one or more vaccines, such as a subunit vaccine or one or more attenuated Gram-negative bacterial strains as described herein. In some embodiments, a single boost is used. In other embodiments, multiple boost immunizations are performed. In particular embodiments drawn to a heterologous prime/boost, a mucosal bacterial prime/parenteral conjugate boost immunization strategy is used. For example, one or more (or all) of the live (or killed) attenuated Gram-negative bacterial strains as taught herein can be administered orally to a subject and the subject can be subsequently boosted parentally with a multivalent conjugate vaccine as described herein.

The time interval between the first and second vaccinations is 1 week, 2 weeks, 3 weeks, 1 month, 2 months, 3 months, 4 months, 5 months, 6 months, 7 months, 8 months, 9 months, 10 months, 11 months, 1 year, 1.5 years and 2 years. Immunization schedules have been scheduled and administered at 1-month intervals, with a priming immunization followed by two sequential booster immunizations.

The particular dosage depends upon the age, weight, sex and medical condition of the subject to be treated, as well as on the method of administration. Suitable doses can be readily determined by those of skill in the art.

The conjugate vaccine of the invention can be administered by either single or multiple doses of an effective amount. In some embodiments, an effective amount of the compositions of the invention can vary from 0.01-5,000 μg/ml per dose. In other embodiments, an effective amount of the composition of certain embodiments can vary from 0.1-500 μg/ml per dose, and in other embodiments, it can vary from 10-300 μg/ml per dose. In one embodiment, the dosage of the conjugate administered will range from about 10 μg to about 1000 μg. In another embodiment, the amount administered will be between about 20 μg and about 500 μg. In some embodiments, the amount administered will be between about 75 g and 250 μg. Greater doses may be administered on the basis of body weight. The exact dosage can be determined by routine dose/response protocols known to one of ordinary skill in the art.

The conjugate vaccine may confer resistance to Gram-negative bacterial infections by either passive immunization or active immunization. In one embodiment of passive immunization, the conjugate vaccine is provided to a subject (i.e. a human or mammal), and the elicited antisera is recovered and directly provided to a recipient suspected of having an infection as described herein.

The administration of the conjugate vaccine (or the antisera which it elicits) may be for either a "prophylactic" or "therapeutic" purpose. When provided prophylactically, the vaccine is provided in advance of any symptom of bacterial infection. The prophylactic administration of the vaccine serves to prevent or attenuate any subsequent infection. When provided therapeutically, the vaccine is provided upon the detection of a symptom of actual infection. The therapeutic administration of the vaccine serves to attenuate any actual infection.

4. Summary of Experimental Results

The following is a summary of results of experiments described in the Examples of this application:
- Constitutive high-level expression of Wzz protein alters the proportion of a defined modal length population of OPS.
- Overexpression of wzzB from *Salmonella enterica* serovar *Typhimurium* CVD 1925 resulted in a shift from low OPS toward an intermediate (long) LPS phenotype, with about 10-fold more long-chain LPA produced relative to CVD 1925 without plasmid, or containing the empty plasmid vector.
- *Salmonella enterica* serovar *Typhimurium* wzzB expressed in *Salmonella enterica* serovar Paratyphi A resulted in OPS production shifted from low-molecular weight to a long-modal length.
- *Salmonella enterica* serovar *Typhimurium* wzzB expressed in *Shigella flexneri* 2a CVD 1208S resulted in OPS produced shifted from a short and very long repeat unit to a uniform high molecular weight species that intermediate between the short and very long O chain length.

5. Examples

The invention is illustrated herein by the experiments described by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Example 1: Materials and Methods

Construction of Safe Attenuated Gram-Negative Bacterial Strains

One aspect of certain embodiments is the construction of clinically well tolerated attenuated strains of *Salmonella enterica* serovar *Typhimurium* and *Salmonella enterica* serovar Paratyphi A for use as live oral vaccines for safer and more economical manufacture as well as using these strains in a heterologous mucosal prime/parenteral boost immunization strategy to broaden both the immunogenicity and protective capacity of the conjugate vaccine. For example, both the guaBA and clpP genes from *Salmonella enterica* serovar *Typhimurium* strain 177 and both the guaBA and clpX genes were deleted from *Salmonella enterica* serovar Paratyphi strain CVD 1902, using a highly efficient site-directed mutagenesis strategy. Deletion of guaBA, clpP or clpX and fljB was achieved by Lambda Red-mediated mutagenesis and was performed as described by Datsenko et al. 2000 (Proc. Natl. Acad. Sci. U.S.A. 97:6640-6645), with modifications (as described by S. Tennant, et al. Infect Immun 2011 79:4175-85 incorporated herein). Deletion regions in the chromosomes of each of the resulting attenuated strains were sequenced to confirm that only the intended genes and DNA sequences had been removed. Further mutations were introduced into fliD to secrete FliC monomers, as well as deleting the fljBA locus encoding phase 2 flagellin FljB and the FliC repressor protein FljA from *Salmonella enterica* serovar *Typhimurium*. For *Shigella flexneri* CVD 1208S, deletions in guaBA, set and sen were created using homologous recombination as described by Kotloff et al 2007 (Human Vaccines 3:628-275). Deletions in guaBA and clpX were introduced in *Salmonella enterica* serovar Newport Chile 361 by homologous recombination using the method of Datsenko and Wanner to obtain *Salmonella enterica* serovar Newport CVD 1962. Detailed discussion of the preparation of safe attenuated Gram-negative bacterial strains shown, but not limited to those in Table 1, for use as reagent strains is also described in U.S. Patent Application Pub. No. 2013/0129776 A1.

Bacterial Strains, Plasmids, and Culture Conditions

Plasmids as described herein in Table 3 were used for chromosomal deletions. (Datsenko et al., 2000 (Proc. Natl. Acad. Sci. U.S.A. 97:6640-6645). Plasmid pCR-Blunt II-TOPO (Invitrogen, Carlsbad, Calif.) was used to clone blunt-ended polymerase chain reaction (PCR) products. *Salmonella* strains were maintained on animal product-free Lennox media (Athena Environmental Sciences, Baltimore, Md.) at 370 Celsius. All bacterial strains were maintained in Hi-Soy (HS) bacteriological media (5 g/L sodium chloride, 10 g/L soytone [Teknova, Hollister, Calif.], 5 g/L Hy-yest [Sigma Aldrich, St. Louis, Mo.]) at 37° C. Growth media for all guaBA mutants were supplemented with guanine (0.001% weight [w]/volume [v]). When required, antibiotics were used at a final concentration of 50 μg/ml kanamycin. Chemically defined medium (Rondin et al., 2011, Clin. Vaccine Immunol. 18:460-468) was prepared by combining 5 ml 1 M $MgSO_4$, 130 μl 0.1 M thiamine hydrochloride, 25 ml 20% glycerol, 5 ml trace salts solution (0.2 g $5H_2O$, 0.08 sodium iodide, 3.00 g $MnSO_4.H_2O$), 0.20 grams $Na2MoO_4.2H_2O$, 0.02 g boric acid, 0.50 g $CoCl_2.6H_2O$, 0.50 g $CaSO_4.2H_2O$, 7.00 g $ZnCl_2$, 22.0 g $FeSO_4.7H_2O$ per liter) with 1 L base solution (13.3 g $KH_2PO_4$, 1.7 g citric acid).

DNA Methods

Plasmid extraction and gel purification of DNA fragments was performed using Wizard (Promega, Madison, Wis.) and QIAquick Gel Extraction (QIAGEN, Valencia, Calif.) kits, respectively, as directed by the manufacturer. All restriction enzymes were purchased from New England Biolabs (Ipswich, Mass.).

PCR amplifications were routinely performed with 1-2.5 U Taq DNA polymerase (Denville Scientific, Metuchen, N.J., or Genscript, Piscataway, N.J.), 1.times.PCR Buffer containing 1.5 mM $MgCl_2$, 200 μM each dNTP and 1 μM of each primer in a reaction volume of 20 to 50 μl in an Eppendorf Mastercycler. For PCRs using long primers (>25 bp) the amount of MgCl$_2$ was increased as necessary. When error-free and/or blunt end PCR products were required, Vent$_R$™ DNA polymerase (New England Biolabs, Ipswich, Mass.) was used according to the manufacturer's instructions.

LPS Isolation and Visualization

Samples were prepared from cultures grown in media without shaking at 37 degrees Celsius. After overnight growth, bacterial cultures were adjusted to an OD$_{600}$ of 1.0 and then 2 ml of culture was centrifuged at maximum speed for 2 minutes at 4° C. The supernatant was removed and the pellet re-suspended in 100 µl lysis buffer (0.1 M Tris-HCl, pH6.8, 2% SDS, 10% Glycerol, 4% 2-mercaptoethanol). The sample was boiled at 95-100° C. for 10 minutes to lyse the cells. Proteins were digested by adding 25 µg Proteinase K. The sample was incubated at 60° C. for 1 hour. The sample was boiled for 10 minutes and then allowed to cool on ice. Twenty microliters of the sample was electrophoresed on 4-15% Mini Protean TGX stain free gels (BioRad Laboratories) with the CandyCane Glycoprotein ladder (Life Technologies). LPS was stained using Pro-Q Emerald 300 LPS Gel Stain (Life Technologies) as per the manufacturer's instructions.

Example 2: Generation of Strains that Overexpress wzzB

Expression of wzzB from a High Copy Number Plasmid

The wzzB gene was first cloned into a high copy number, ampicillin-resistant plasmid pSE280. wzzB was amplified from *Salmonella enterica* serovar *Typhimurium* 177 using primers

```
wzzBF-BamHI:
                                    (SEQ ID NO. 1)
5' AAAGGATCCATGACAGTGGATAGTTATACG 3'
and wzzB-PstI:
                                    (SEQ ID. NO. 2)
5' AAACTGCAGTTACAAGGCTTTTGGCTTATAG 3'.
```

The 1 kb-PCR product was purified using a QIAQUICK PCR Purification Kit (Qiagen) and then digested with BamHI and PstI. The digested product was ligated to similarly digest pSE280 and electroporated into *E. coli* DH5alpha. pSE280-wzzB plasmid DNA was isolated and the plasmid was subsequently electroporated into bacterial strains of interest.

Expression of wzzB from a Low Copy Number Plasmid wzzB was cloned from pSE280-wzzB into pSEC10, a non-transmissible low copy number expression plasmid which encodes resistance to kanamycin. A 984-bp-fragment encoding wzzB was inserted as a BamHI-NheI fragment into pSEC10 cleaved with BamHI and NheI. The resultant plasmid pSEC10-wzzB is 7275 base pairs (bp).

Example 4: Plasmid Construction

Figure 3:
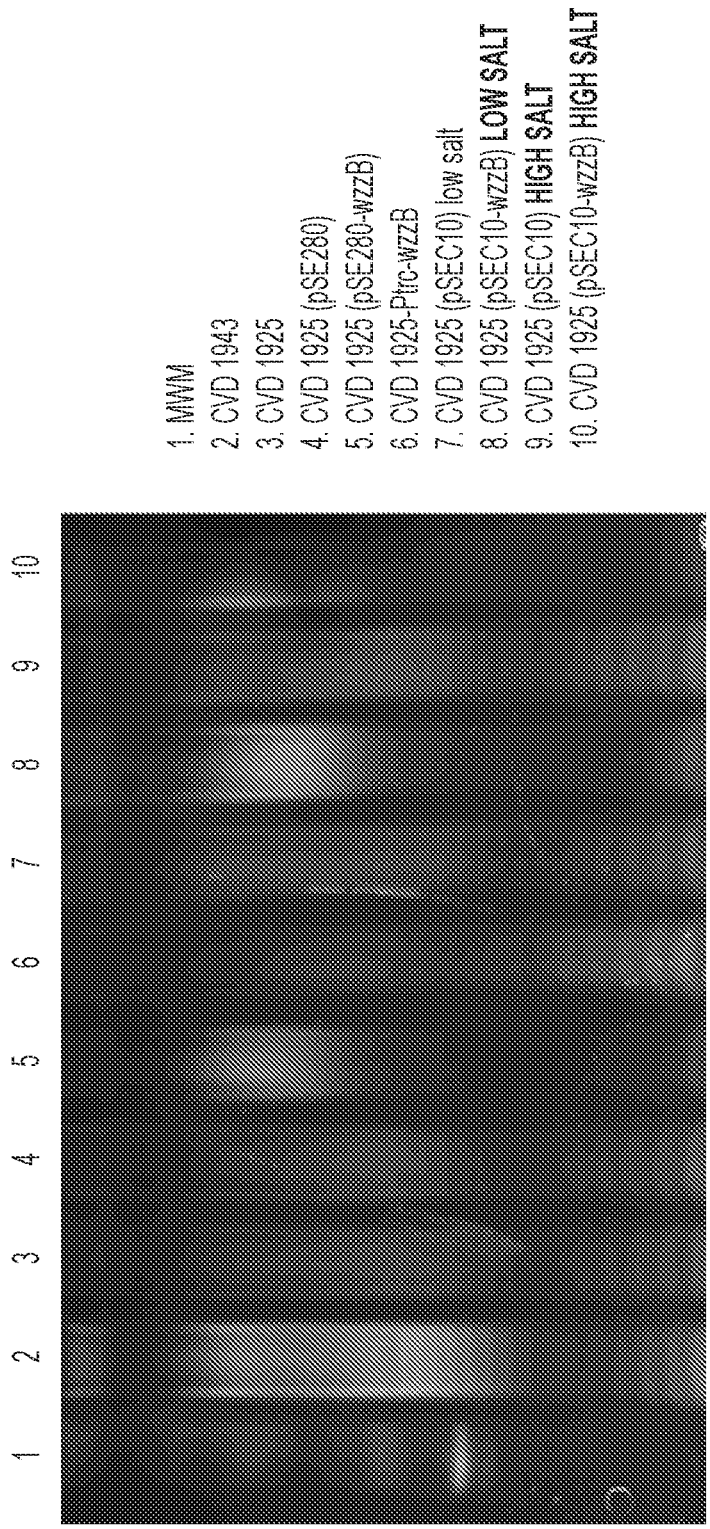
FIG. 3 is a photograph illustrating visualization of LPS produced by *Salmonella enterica* serotype *Typhimurium* CVD 1925 over-expressing wzzB. The wzzB gene was expressed from the chromosome and from two different plasmids, pSE280 (high copy number, ampicillin resistant, Ptrc promoter) and pSEC10 (low copy number, kanamycin resistant, PompC promoter [salt inducible]). LPS micro preparations from whole cells were separated by SDS-PAGE and stained for polysaccharide. *Salmonella enterica* serotype *Enteritidis* LPS was included as a control. Lane descriptions are indicated. Where applicable, high and low salt media growth conditions are indicated; according to an embodiment.

The 7275-base pair (bp)-plasmid pSEC10-wzzB is a non-transmissible low copy number expression plasmid which encodes resistance to kanamycin. pSEC10-wzzB also carries the 984-bp-gene wzzB that encodes a 36.3 kDa (327 amino acid) WzzB protein which controls the chain length of O-polysaccharide. pSEC10-wzzB was constructed using the original expression plasmid pSEC10 (Stokes et al. 2007. Infection and Immunity. 75(4): 1827-34). To construct pSEC10-wzzB, a 984-bp-fragment encoding wzzB was inserted as a BamHI-NheI fragment into pSEC10 cleaved with BamHI and NheI (FIG. 2), Example 5: Overexpression of wzzB in the Homologous Organism In order to assess whether constitutive high-level expression of a homologous Wzz protein could alter the proportion of a defined modal length population, the WzzB protein from *Salmonella Typhimurium* was expressed in a strain of *Salmonella Typhimurium* that was demonstrated to produce predominantly low OPS repeats. Expression of wzzB from *Salmonella Typhimurium* CVD 1925 (177 ΔguaBA ΔclpP ΔfliD ΔfljB) resulted in a shift towards the intermediate (long) LPS phenotype, with about 10-fold more long-chain LPS produced relative to CVD 1925 without plasmid, or containing the empty plasmid vector (FIG. 3). Comparable results were found when wzzB was expressed from high-copy (pSE280) and low-copy (pSEC10) plasmids.

Figure 5:
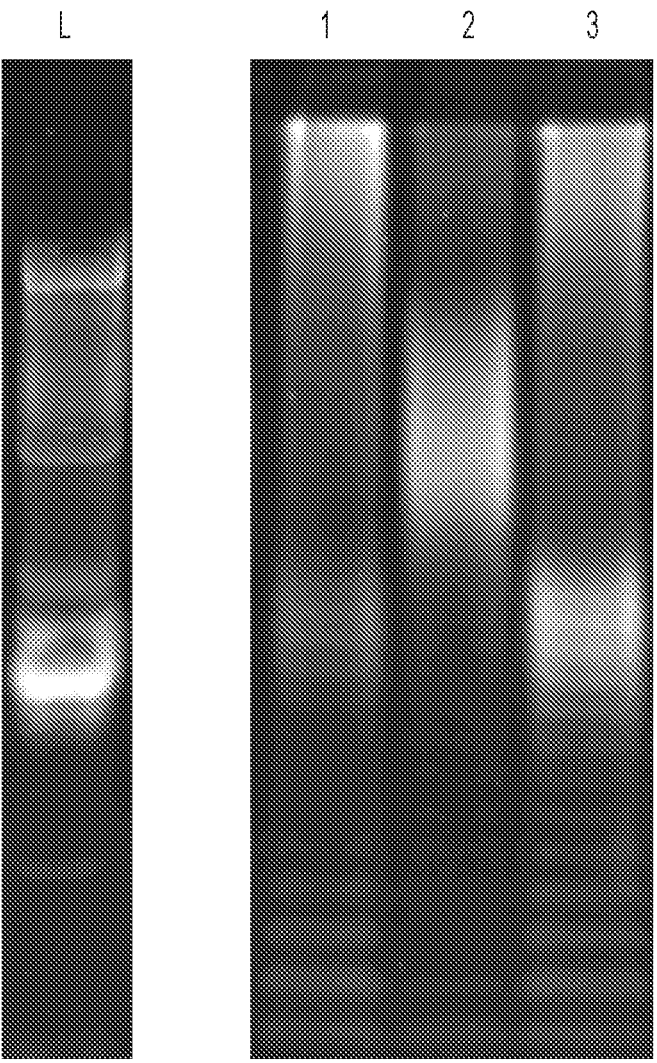
FIG. 5 is a photograph illustrating visualization of LPS produced by *Shigella flexneri* CVD 1208S over-expressing wzzB. The wzzB gene was expressed from pSEC10. LPS micro preparations from whole cells were separated by SDS-PAGE and stained for polysaccharide. Lane descriptions are indicated; according to an embodiment.

Example 6: Heterologous Expression in Other Serovars of the Same Species and Other Species Using the Wzy System In order to test whether expression of a Wzz protein could confer similar modal length changes in other bacteria that use the Wzy system and express varying modal length LPS, the plasmids expressing wzzB from *Salmonella enterica* serovar *Typhimurium* were used to transform a heterologous *Salmonella* serovar (*Salmonella* Paratyphi A), as well as a heterologous bacterial species (*Shigella flexneri* 2a). When the *Salmonella enterica* serovar *Typhimurium* wzzB was expressed in *Salmonella enterica* serovar Paratyphi A, the OPS produced was similarly shifted almost entirely from low-molecular weight to a long modal length (FIG. 4). When wzzB from *Salmonella enterica* serovar *Typhimurium* was expressed in *Shigella flexneri* 2a CVD 1208S, a modal shift was seen from short and very long repeat containing OPS, to a uniform high molecular weight species that was intermediate between the short and very long O chain length (FIG. 5).

Example 7: Overexpression of wzzB in *Salmonella* Newport CVD 1962

Figure 6:
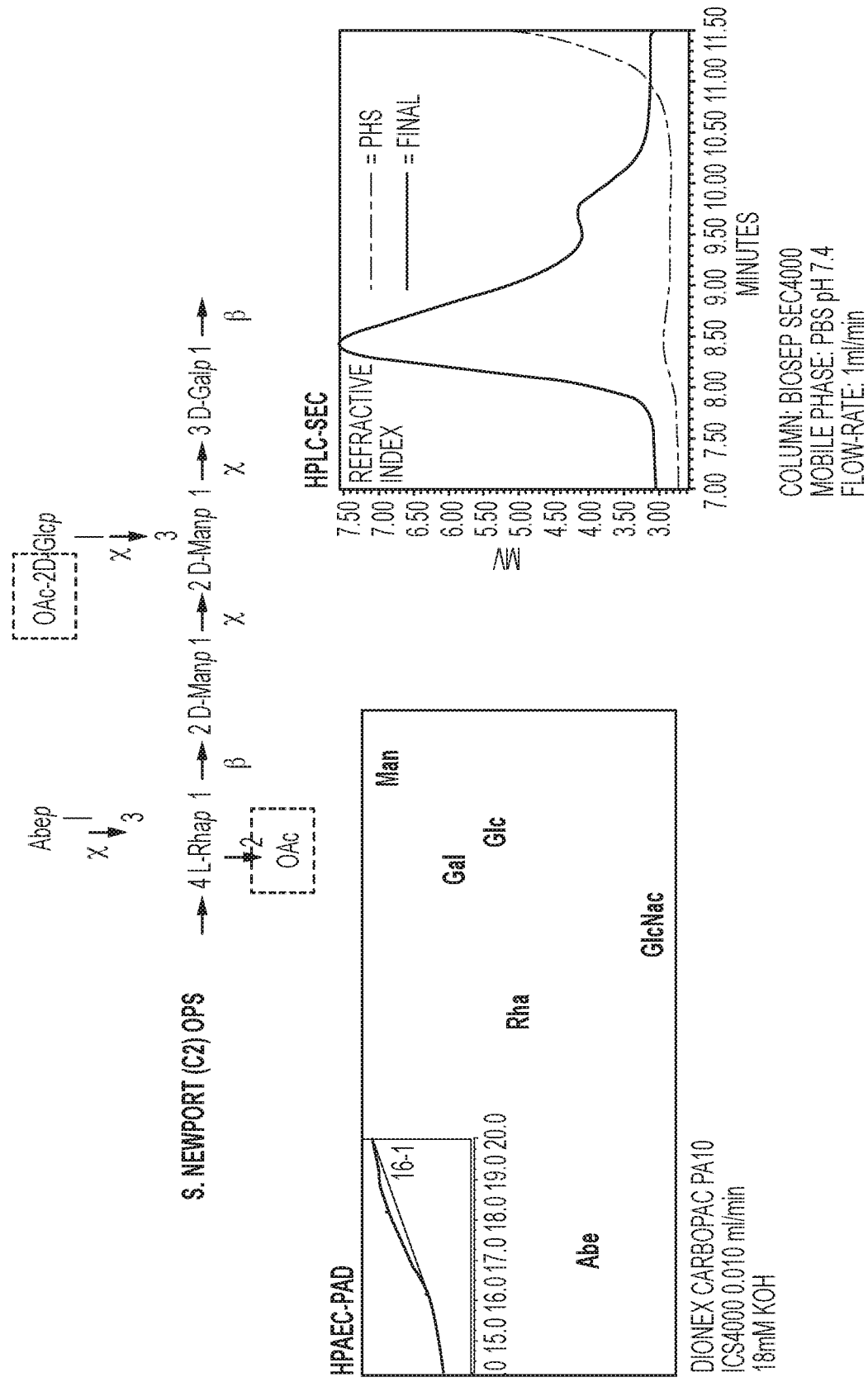
FIG. 6 is a schematic diagram illustrating characterization of purified native COPS from *Salmonella enterica* serotype Newport CVD 1962; according to an embodiment.
Figure 7:
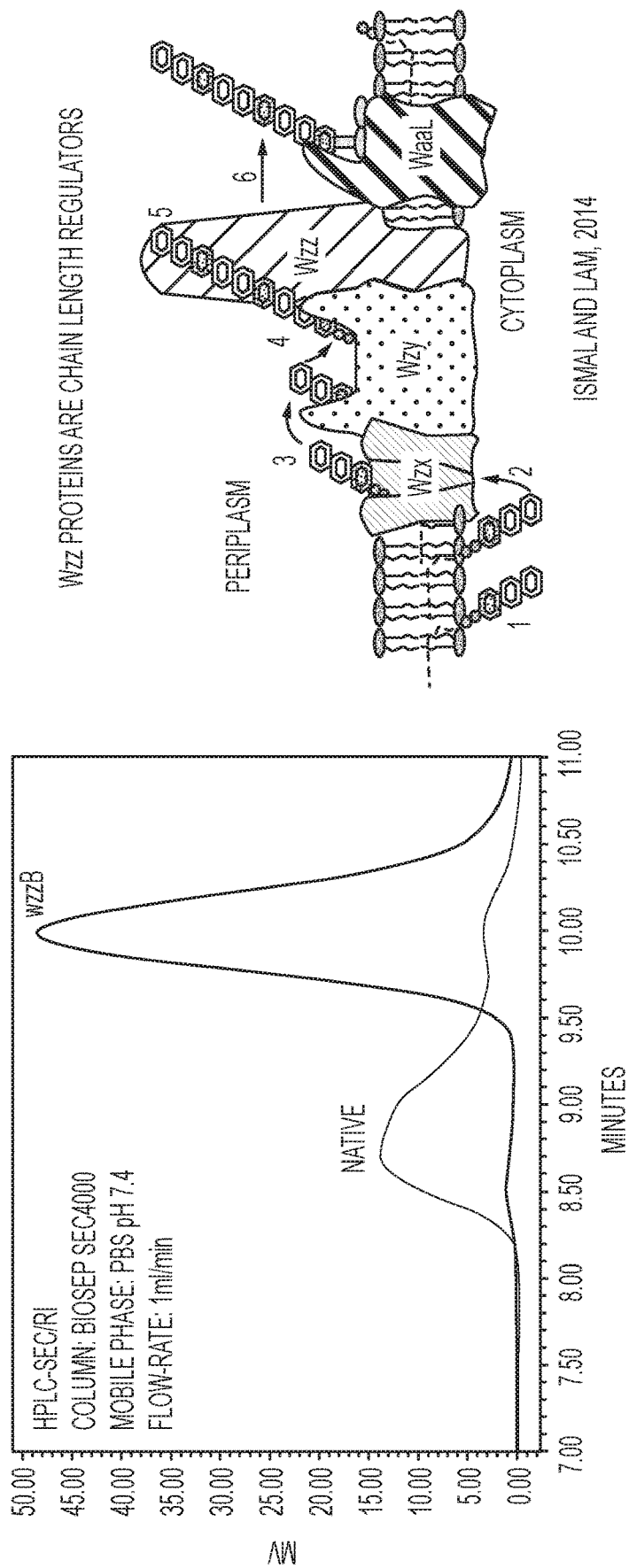
FIG. 7 is a schematic diagram illustrating characterization of purified native COPS form *Salmonella enterica* serotype Newport CVD 1962 (very-long+long chain length) vs. COPS from *Salmonella enterica* serotype Newport wzzB CVD 1966 (long-chain only); according to an embodiment.
Figure 8:
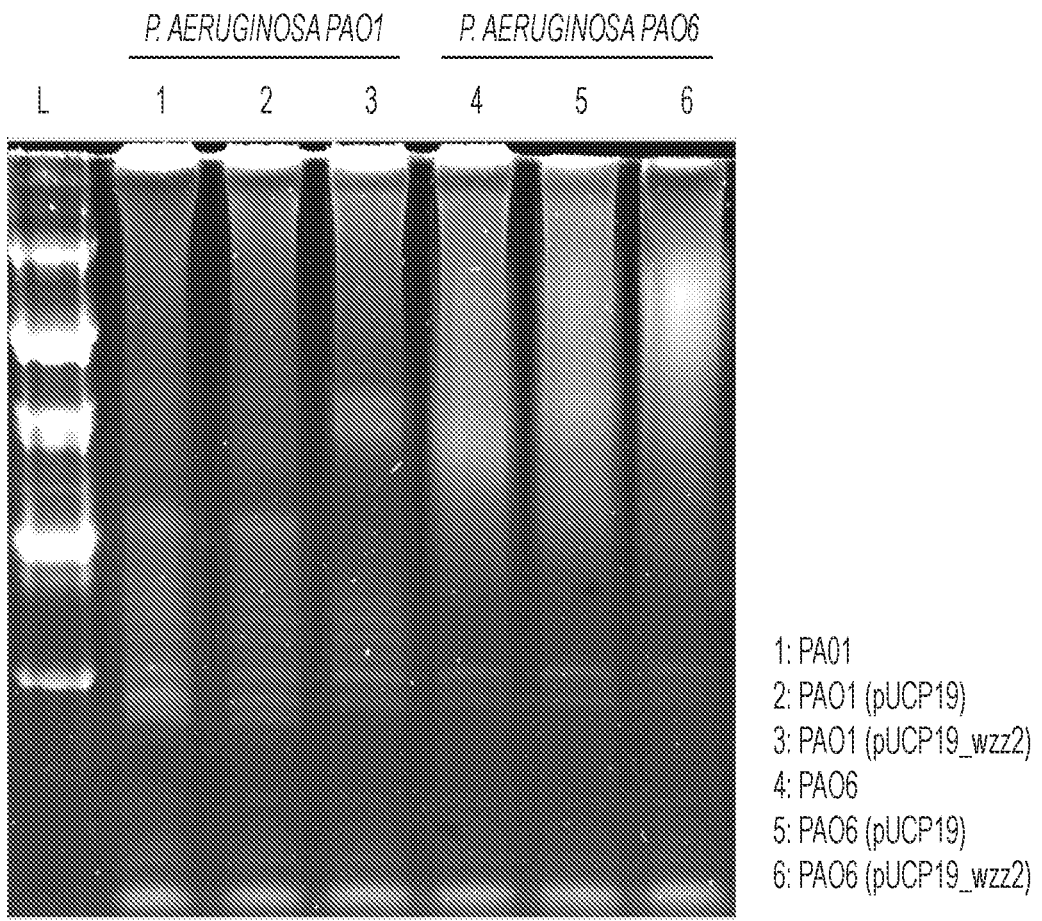
FIG. 8 is a photograph of a Western Blot gel illustrating overexpression of wzz2 from *Pseudomonas aeruginosa* in various *Pseudomonas* strains; according to an embodiment.
Figure 9:
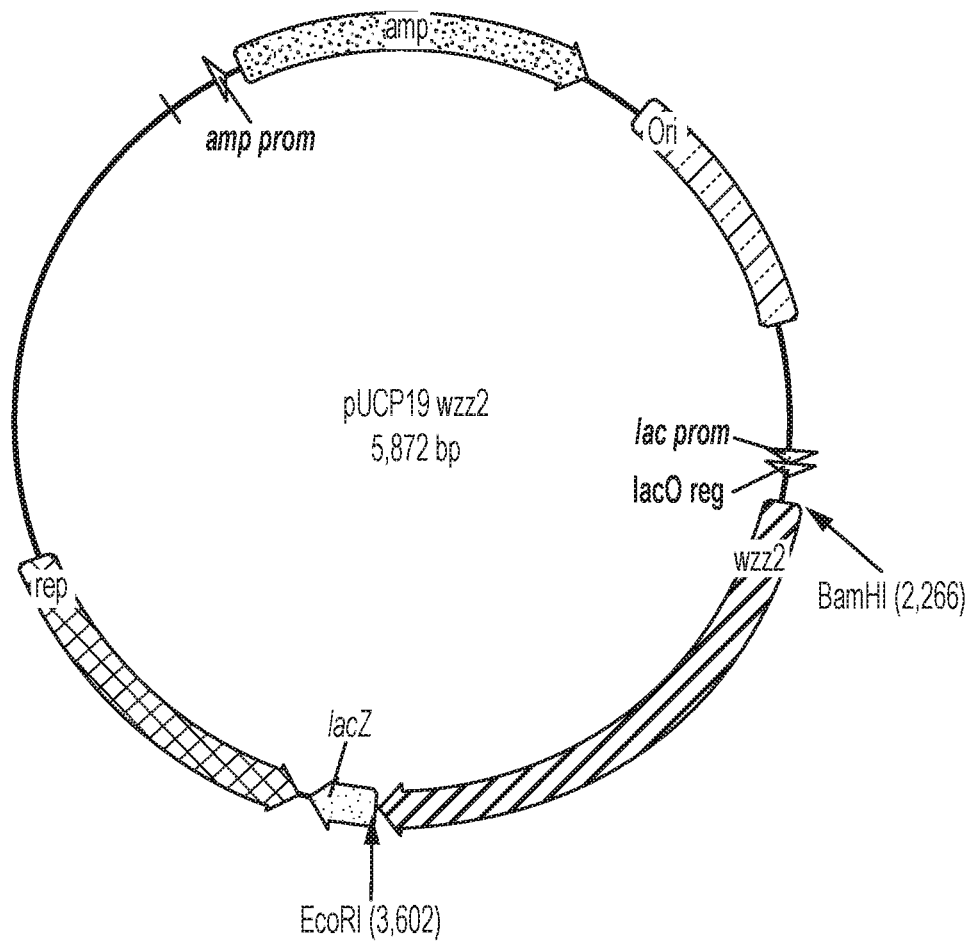
FIG. 9 is a schematic diagram of a pUC19wzz2 expression plasmid. The wzz2 gene was cloned downstream from the amp promoter in the ampicillin-resistant plasmid pUCP19wzz2.
Figure 10:
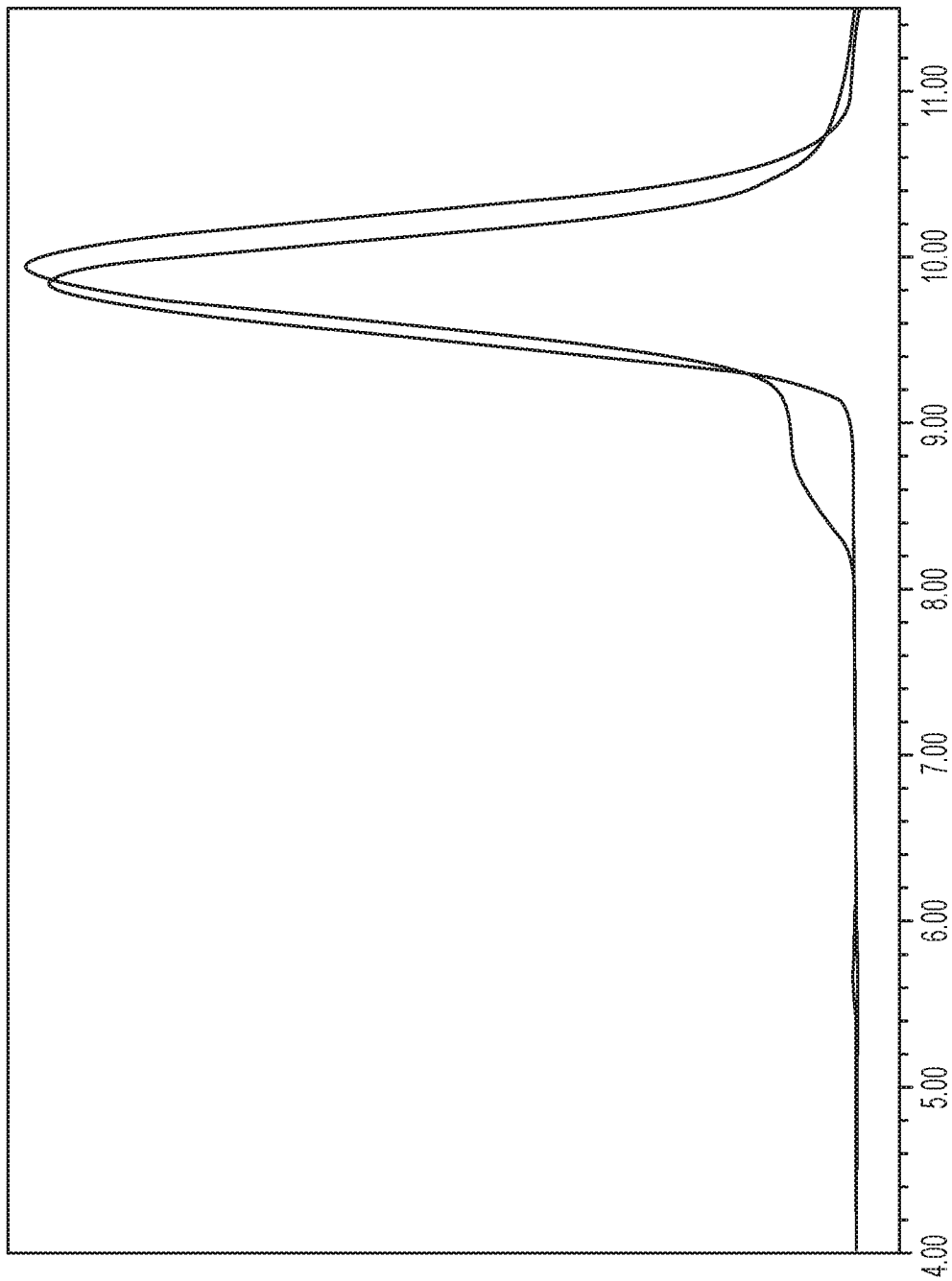
FIG. 10 is a schematic diagram illustrating producing an identifiable peak by HPLC-SEC indicating soluble released polysaccharide that was separated from residual impurities that were all lower molecular weight; according to an embodiment.
Figure 11:
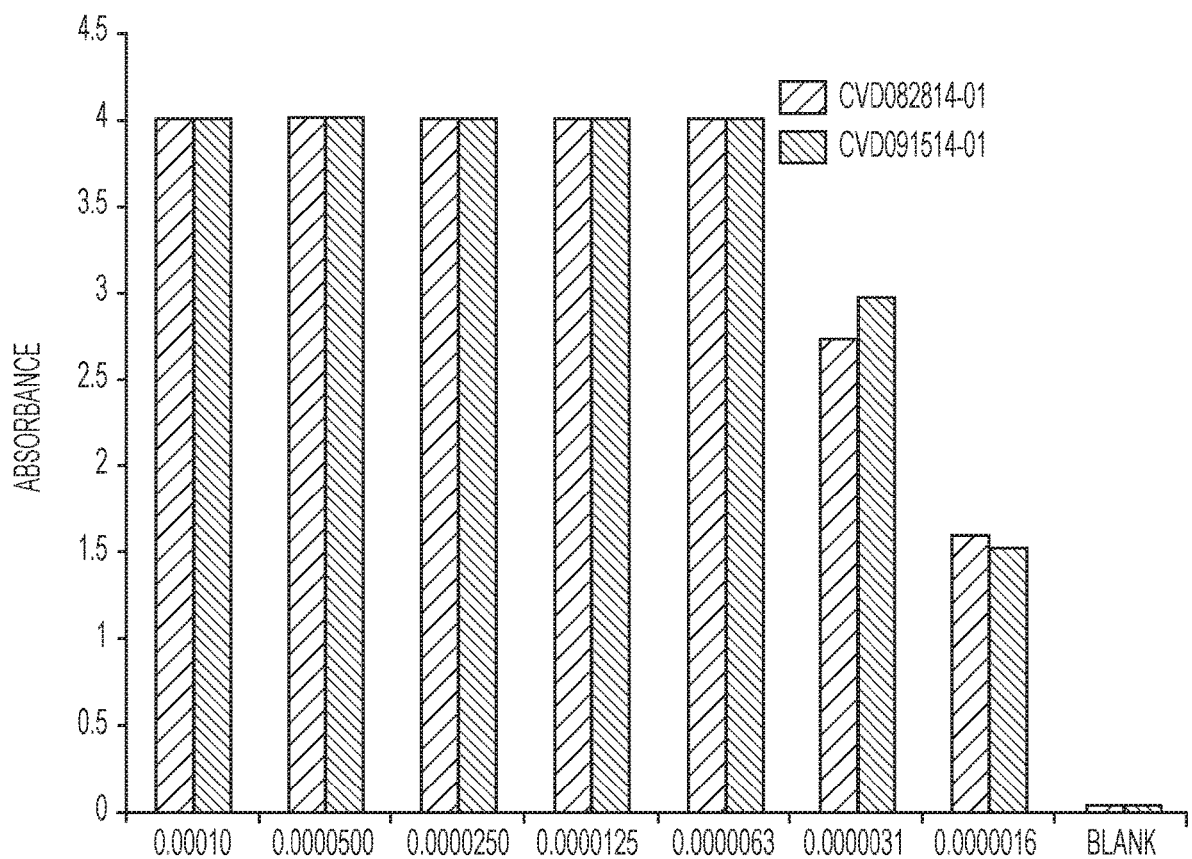
FIG. 11 is an HPLC-SEC analysis of COPS purified from *Salmonella enterica* serotype *Typhimurium* CVD 1925 and *Shigella flexneri* CVD 108S overexpressing wzzB. Purified COPS from *Salmonella enterica* serotype *Typhimurium* CVD 1925 pSEC10-wzzB (thin gray line) and CVD 1208S pSEC10-wzzB (thick black line) were separated by HPLC-SEC and detected by refractive index; according to an embodiment.
Figure 12:
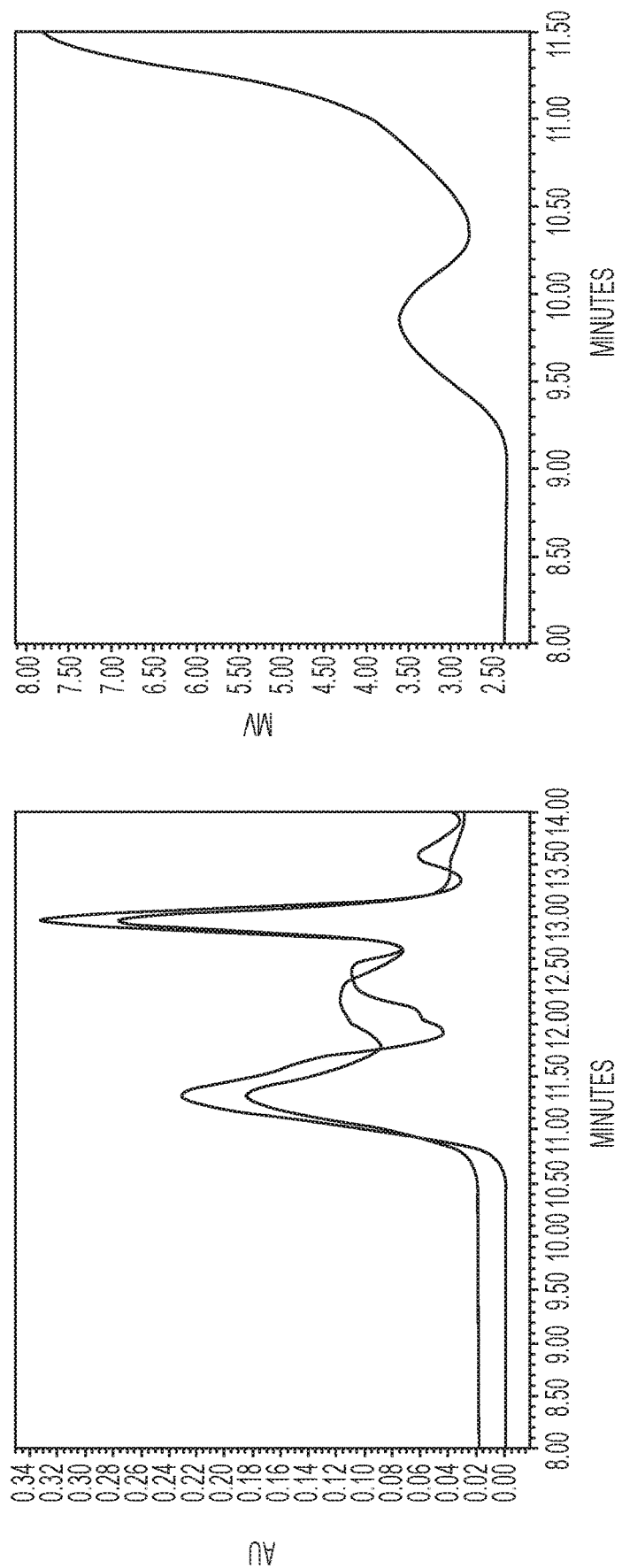
FIG. 12 is an illustration providing recognition of COPS purified from *Salmonella enterica* serotype *Typhimurium* CVD 1925 overexpressing wzzB by a type-specific monoclonal antibody. COPS from independent lots were assessed by direct ELISA using various dilutions of a serogroup-specific anti-O epitope 4 monoclonal antibody.

When wzzB from *Salmonella enterica* serovar *Typhimurium* was expressed in *Salmonella enterica* serovar Newport CVD 1962 (harbors mutations in guaBA and clpX), using plasmid pSEC10, we observed an increase in O antigen length. Purified native COPS from *Salmonella enterica* serovar Newport CVD 1962 was characterized as shown in FIG. 6. A comparison was conducted between purified native COPS from *Salmonella enterica* serovar Newport CVD 1962 (very-long+long chain length) vs. COPS from *Salmonella enterica* serovar Newport wzzB CVD 1966 (possesses mutations in guaBA and htrA and expresses long-chain O antigen only). *Salmonella enterica* serovar *Typhimurium* wzzB (long-chain length OPS) overexpressed in *Salmonella enterica* serovar Newport generated a >98% production of long-chain length COPS (FIG. 7).

Example 8. Purification and Characterization of COPS from *Salmonella enterica* Serovar *Typhimurium*

*Salmonella enterica* serovar *Typhimurium* COPS for use as vaccine antigen and for ELISA analyses was purified from reagent strain CVD 1925 wzzB, an attenuated vaccine strain that was engineered to express long-chain OPS (16-35 repeating units) due to overexpression of wzzB, a member of the polysaccharide co-polymerase family. COPS purified from CVD 1925 wzzB (STm COPS) demonstrated a single, sharply-defined population that was determined to be 19.8 kDa by SEC-MALS analysis. HPAEC-PAD analysis confirmed the presence of expected O12 monosaccharides, and glucosylation at ~21% of OPS repeats based on the ratio with rhamnose. Purified STm COPS was recognized by monoclonal antibodies against the O4 and O5 epitopes. 1H and 13C NMR indicated variable O-acetylation at abequose C2 and C2/3 of rhamnose. A comparable pattern of glucosylation and O-acetylation was found for the OPS of *Salmonella enterica* serovar *Typhimurium* strain D65, a previously described Malian *Salmonella enterica* serovar *Typhimurium* ST313 clinical isolate that was used herein for challenge studies in mice. D65 COPS demonstrated a bimodal size distribution with a population that was equivalent in size to CVD 1925 wzzB COPS, as well as a higher molecular weight species. Polysaccharide O-acetyl groups are stable at neutral pH, but labile under alkaline conditions. In order to assess the site-specific susceptibility of the O-acetyl groups to base treatment, residual O-acetylation at these positions was assessed after exposure to different pH conditions. It was found that O-acetylation was maintained at pH 7 and pH 8, but that O-acetyl groups were removed at approximately equivalent levels from abequose and rhamnose at pH levels greater than 9. ELISA analyses with anti-O4 and O5 monoclonal antibodies confirmed that pH 10 treatment resulted in marked loss of the O5 epitope while maintaining O4 antigenicity.

Example 9. Immunogenicity and Protective Activity of *S. Typhimurium* COPS: Flagellin Glyconjugates Synthesized with Different Chemistries Conjugates of purified STm COPS and *Salmonella enterica* serovar *Typhimurium* phase 1 flagellin (FliC) were generated by different strategies. Lattice conjugates were initially generated by multipoint conjugation between random STm COPS polysaccharide hydroxyls and amino groups on ADH-derivatized flagellin proteins using CDAP cyanylation chemistry (STm COPS$^{Lat}$:FliC). Accordingly, while efficient formation of high molecular weight conjugates was observed it was found that there was a marked loss of polysaccharide O-acetyls after conjugation. Mice immunized with this conjugate generated significant levels of anti-COPS IgG compared to controls administered PBS; however the geometric mean titers (GMTs) were low and no difference was seen when the sera were assessed with STm dOAc-COPS. Infection with $1\times10^5$ or $5\times10^5$ CFU of *Salmonella enterica* serovar *Typhimurium* D65 produced 70% and 100% mortality respectively in unimmunized controls whereas immunization with the STm COPS$^{Lat}$:FliC conjugate provided 43% (P=0.11) and 30% (P=0.0202) protection against these challenge levels.

In order to produce a conjugate formulation that retained OPS O-acetyls, sun-type conjugates were generated by functionalization of the STm COPS reducing end KDO carbonyl by oximation with an aminooxy thiol reagent to form a free thiol that was then coupled to maleimide derivatized protein lysines (STm COPS$^{KDO}$:FliC). This approach allowed the entire conjugation to be performed at approximately neutral pH. Conjugates generated by this method maintained levels of O-acetylation comparable with the native polysaccharide. Mice immunized with STm COPS$^{KDO}$:FliC manifested robust anti-STm COPS IgG titers for which the GMT was ~1,000-fold higher than that achieved with the lattice conjugate. Titers to native STm COPS were ~10-fold higher than those directed against dOAc STm COPS, and thus similar to the profile found for sera from mice immunized with CVD 1931. Immunization with this conjugate also induced high anti-flagellin titers in all mice that were comparable to those achieved after immunization with unconjugated flagellin. Mice immunized with STm COPS$^{KDO}$:FliC were markedly protected against fatal challenge with *Salmonella enterica* serovar *Typhimurium* D65. Infection at the high ($5\times10^5$ CFU) and low ($1\times10^5$ CFU) D65 challenge doses in this experiment were sufficient to cause >90% mortality in unimmunized controls, with mice that received the higher dose succumbing more rapidly. Mice immunized with STm COPS$^{KDO}$:FliC were fully (100% vaccine efficacy, P<0.0001) or partially (95% vaccine efficacy, P<0.0001) protected against fatal infection at these low and high challenge doses respectively.

REFERENCES

All references cited herein are hereby incorporated by reference in their entirety.
1. Simon R, Tennant S M, Wang J Y, Schmidlein P J, Lees A, et al. (2011) *Salmonella enterica* serovar *enteritidis* core O-polysaccharide conjugated to H:g,m flagellin as a candidate vaccine for protection against invasive infection with *S. enteritidis*. Infect Immun 79: 4240-4249.
2. Watson D C, Robbins J B, Szu S C (1992) Protection of mice against *Salmonella typhimurium* with an O-specific polysaccharide-protein conjugate vaccine. Infect Immun 60: 4679-4686.
3. Cohen D, Ashkenazi S, Green M S, Gdalevich M, Robin G, et al. (1997) Double-blind vaccine-controlled randomised efficacy trial of an investigational *Shigella sonnei* conjugate vaccine in young adults. Lancet 349: 155-159.
4. Bardotti A, Averani G, Berti F, Berti S, Carinci V, et al. (2008) Physicochemical characterisation of glycoconjugate vaccines for prevention of meningococcal diseases. Vaccine 26: 2284-2296.
5. Svenson S B, Lindberg A A (1981) Artificial *Salmonella* vaccines: *Salmonella typhimurium* O-antigen-specific oligosaccharide-protein conjugates elicit protective antibodies in rabbits and mice. Infect Immun 32: 490-496.
6. Robbins J B, Kubler-Kielb J, Vinogradov E, Mocca C, Pozsgay V, et al. (2009) Synthesis, characterization, and immunogenicity in mice of *Shigella sonnei* O-specific oligosaccharide-core-protein conjugates. Proc Natl Acad Sci USA 106: 7974-7978.
7. Kubler-Kielb J, Vinogradov E, Mocca C, Pozsgay V, Coxon B, et al. (2010) Immunochemical studies of *Shigella flexneri* 2a and 6, and *Shigella dysenteriae* type 1 O-specific polysaccharide-core fragments and their protein conjugates as vaccine candidates. Carbohydr Res 345: 1600-1608.
8. Lindberg A A, Le Minor L (1984) Serology of *Salmonella*. In: Bergan T, editor. Methods in Microbiology: Academic Press. pp. 1-141.
9. Carter J A, Jimenez J C, Zaldivar M, Alvarez S A, Marolda C L, et al. (2009) The cellular level of O-antigen polymerase Wzy determines chain length regulation by WzzB and WzzpHS-2 in *Shigella flexneri* 2a. Microbiology 155: 3260-3269.
10. Islam S T, Lam J S (2014) Synthesis of bacterial polysaccharides via the Wzx/Wzy-dependent pathway. Can J Microbiol 60: 697-716

What is claimed is:

1. A *Salmonella enterica* serotype *Typhimurium* CVD 1925 core-O-polysaccharide hapten purified from *Salmonella enterica* serotype *Typhimurium* CVD 1925 which overexpresses a *Salmonella enterica* serotype *Typhimurium* wzz family protein.

2. The core-O-polysaccharide hapten of claim 1, wherein the wzz family protein is wzzB.

3. The core-O-polysaccharide hapten of claim 1, further comprising a carrier protein.

4. The conjugate or complexed vaccine of claim 3, wherein the core-O-polysaccharide hapten is covalently linked or complexed to a carrier protein.

5. The conjugate or complexed vaccine of claim 3, wherein the core-O-polysaccharide hapten and the carrier protein are chemically conjugated or complexed using a cross-linker or polymer.

6. The conjugate vaccine of claim 3, wherein the carrier protein is from a homologous bacterial strain or a heterologous bacterial strain.

7. The conjugate vaccine of claim 3, wherein the carrier protein is flagellin and selected from the group consisting of flagellin A, flagellin B, phase 1 flagella protein, and phase 2 flagella protein.

8. The conjugate vaccine of claim 7, wherein the flagellin is from the homologous or a heterologous species as the core-O-polysaccharide hapten.

9. The core-O-polysaccharide hapten of claim 1, formulated as a conjugate vaccine or a complexed vaccine.

\* \* \* \* \*

UNITED STATES PATENT AND TRADEMARK OFFICE
CERTIFICATE OF CORRECTION

PATENT NO. : 10,716,839 B2
APPLICATION NO. : 15/566333
DATED : July 21, 2020
INVENTOR(S) : Tennant et al.

Page 1 of 1

It is certified that error appears in the above-identified patent and that said Letters Patent is hereby corrected as shown below:

On the Title Page

Item (12), should read:
Tennant

Item (72) under Inventors:, should read in full:
Inventors: Sharon M. Tennant, Baltimore, MD (US); Raphael Simon, Baltimore, MD (US); Myron M. Levine, Columbia, MD (US)

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*